(12) United States Patent
Konesky et al.

(10) Patent No.: US 12,102,370 B2
(45) Date of Patent: Oct. 1, 2024

(54) SKIN STATUS MONITOR AND METHOD THEREOF FOR ELECTROSURGICAL APPARATUSES

(71) Applicant: Apyx Medical Corporation, Clearwater, FL (US)

(72) Inventors: Gregory A. Konesky, Hampton Bays, NY (US); Claes Fredrik Jonsson, St. Petersburg, FL (US); Shawn D. Roman, Safety Harbor, FL (US)

(73) Assignee: Apyx Medical Corporation, Clearwater, FL (US)

( * ) Notice: Subject to any disclaimer, the term of this patent is extended or adjusted under 35 U.S.C. 154(b) by 872 days.

(21) Appl. No.: 16/963,389

(22) PCT Filed: Jan. 22, 2019

(86) PCT No.: PCT/US2019/014542
§ 371 (c)(1),
(2) Date: Jul. 20, 2020

(87) PCT Pub. No.: WO2019/147568
PCT Pub. Date: Aug. 1, 2019

(65) Prior Publication Data
US 2021/0007786 A1   Jan. 14, 2021

Related U.S. Application Data

(60) Provisional application No. 62/620,551, filed on Jan. 23, 2018.

(51) Int. Cl.
*A61B 18/00*   (2006.01)
*A61B 18/02*   (2006.01)

(52) U.S. Cl.
CPC ...... *A61B 18/0218* (2013.01); *A61B 2018/00583* (2013.01); *A61B 2018/00595* (2013.01);
(Continued)

(58) Field of Classification Search
None
See application file for complete search history.

(56) References Cited

U.S. PATENT DOCUMENTS 6,109,268 A * 8/2000 Thapliyal ........... A61B 18/1485
606/41
2002/0019627 A1* 2/2002 Maguire ............ A61B 18/1492
606/41

(Continued)

FOREIGN PATENT DOCUMENTS

DE    102012103362 A1   10/2013
EP        3205301 A1    8/2017
WO     2017162614 A1    9/2017

OTHER PUBLICATIONS

Acoustic compliance, inertance and impedance proof of date (Year: 2023).*

(Continued)

*Primary Examiner* — Michael F Peffley
*Assistant Examiner* — Nicholas S Borsch
(74) *Attorney, Agent, or Firm* — Michael J Porco; Gerald E Hespos

(57) ABSTRACT

A skin status monitoring apparatus that includes one or more sensors for sensing the applied energy density to an operative site in real time based on one or more monitored variables is provided. Based on the sensed applied energy density, the applied power level of the cold plasma beam may be adjusted, such that, the applied energy density to the operative site remains within the beneficial range that achieves the desired physiological effect to the operative site. The skin status monitoring apparatus of the present disclosure may be coupled to a distal end of an electrosurgical device capable of generating cold plasma.

22 Claims, 23 Drawing Sheets

(52) U.S. Cl.
CPC ............. *A61B 2018/00601* (2013.01); *A61B 2018/00702* (2013.01); *A61B 2018/00779* (2013.01); *A61B 2018/00791* (2013.01); *A61B 2018/00875* (2013.01)

(56) References Cited

U.S. PATENT DOCUMENTS

| | | | |
|---|---|---|---|
| 2002/0161362 A1* | 10/2002 | Penny | H05H 1/466 |
| | | | 606/41 |
| 2004/0210279 A1 | 10/2004 | Gruzdev | |
| 2006/0189974 A1* | 8/2006 | Penny | A61B 18/042 |
| | | | 606/41 |
| 2007/0232871 A1 | 10/2007 | Sinofsky | |
| 2008/0058782 A1* | 3/2008 | Frangineas | A61B 18/203 |
| | | | 606/9 |
| 2008/0183251 A1 | 7/2008 | Azar | |
| 2008/0237484 A1 | 10/2008 | Morfill et al. | |
| 2009/0076505 A1 | 3/2009 | Arts | |
| 2009/0234351 A1* | 9/2009 | Desinger | A61B 18/1206 |
| | | | 606/34 |
| 2010/0130972 A1* | 5/2010 | Yambor | A61B 18/14 |
| | | | 607/2 |
| 2010/0256618 A1 | 10/2010 | Sakurazawa | |
| 2011/0060270 A1 | 3/2011 | Eppstein | |
| 2011/0140607 A1* | 6/2011 | Moore | H05H 1/36 |
| | | | 315/111.21 |
| 2012/0059255 A1* | 3/2012 | Paul | A61B 18/14 |
| | | | 600/431 |
| 2012/0283732 A1* | 11/2012 | Lam | A61B 17/00491 |
| | | | 606/49 |
| 2012/0310241 A1 | 12/2012 | Orszulak | |
| 2013/0278930 A1 | 10/2013 | Liu et al. | |
| 2013/0345620 A1* | 12/2013 | Zemel | H05H 1/2418 |
| | | | 604/24 |
| 2013/0345670 A1 | 12/2013 | Rajagopalan et al. | |
| 2014/0005665 A1* | 1/2014 | Konesky | A61B 18/10 |
| | | | 606/41 |
| 2014/0074090 A1 | 3/2014 | Lam et al. | |
| 2014/0316403 A1 | 10/2014 | Konesky et al. | |
| 2015/0069911 A1* | 3/2015 | Nettesheim | H01J 37/241 |
| | | | 315/111.21 |
| 2015/0360058 A1* | 12/2015 | Barthe | A61N 7/02 |
| | | | 606/27 |
| 2016/0074116 A1 | 3/2016 | Varghese et al. | |
| 2016/0128755 A1 | 5/2016 | Ho et al. | |
| 2016/0278856 A1* | 9/2016 | Panescu | A61B 5/068 |
| 2016/0287310 A1 | 10/2016 | Nettesheim et al. | |
| 2017/0094769 A1 | 3/2017 | Eckert et al. | |
| 2017/0209707 A1 | 7/2017 | Casalino et al. | |
| 2019/0000542 A1* | 1/2019 | Davison | A61B 18/1477 |
| 2019/0104605 A1 | 4/2019 | Abeelen et al. | |
| 2020/0315729 A1* | 10/2020 | Blanco | F16H 21/54 |

OTHER PUBLICATIONS

University of New South Wales, Acoustic compliance, inertance and impedance, Oct. 14, 2010 (Year: 2010).*
Annotated Yambor Fig 9 (Year: 2023).*
BTLmedical: "Epicondylitis Treatment Using BTL High Intensity Laser", YouTube, May 29, 29816 (2816-85-29), p. 1, XP854979728, Retrieved from the Internet: URL:https://www.youtube.com/watch?v=eP6PMW aNW8k [retrieved on 2019-89-38].
EP Search Report and Written Opinion for EP Application No. 19 744 291.6; dated Jul. 30, 2021; eleven (11) pages.
International Search Report and Written Opinion for PCT Application No. PCT/US2019/014542; dated Apr. 9, 2019, 2018; nine (9) pages.
BTL Medical "Epicondylitis Treatment Using BTL High Intensity Laser" May 29, 2016. Retrieved from the Internet [Mar. 14, 2019] URL: https:/lwww.youtube.comlwatch?v=eP6PMWaNW8k.

* cited by examiner

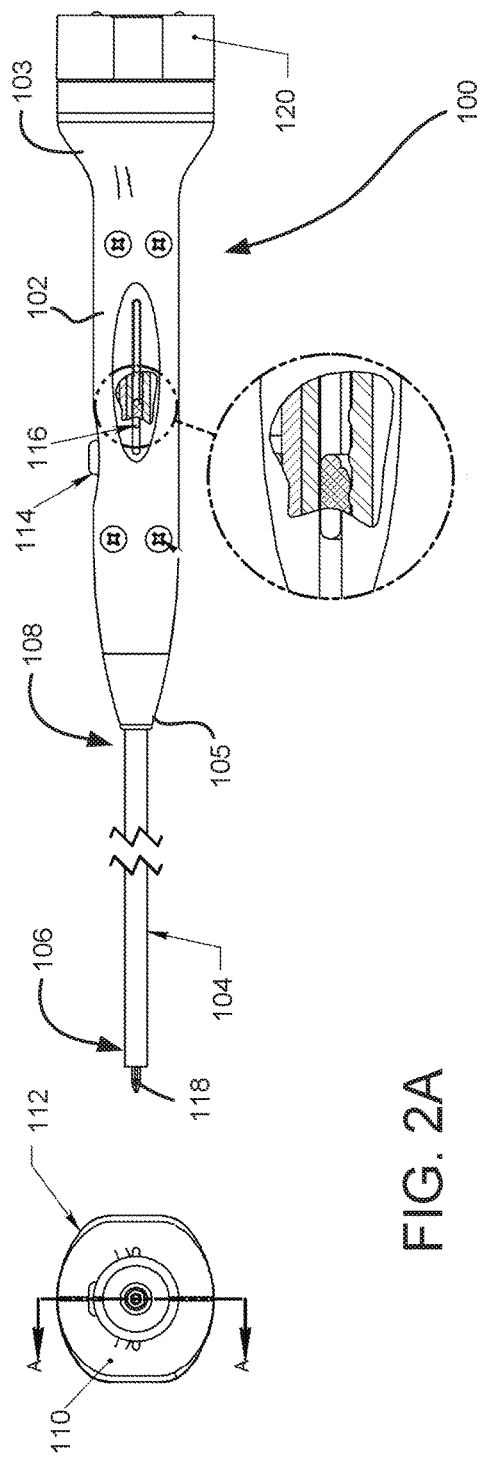
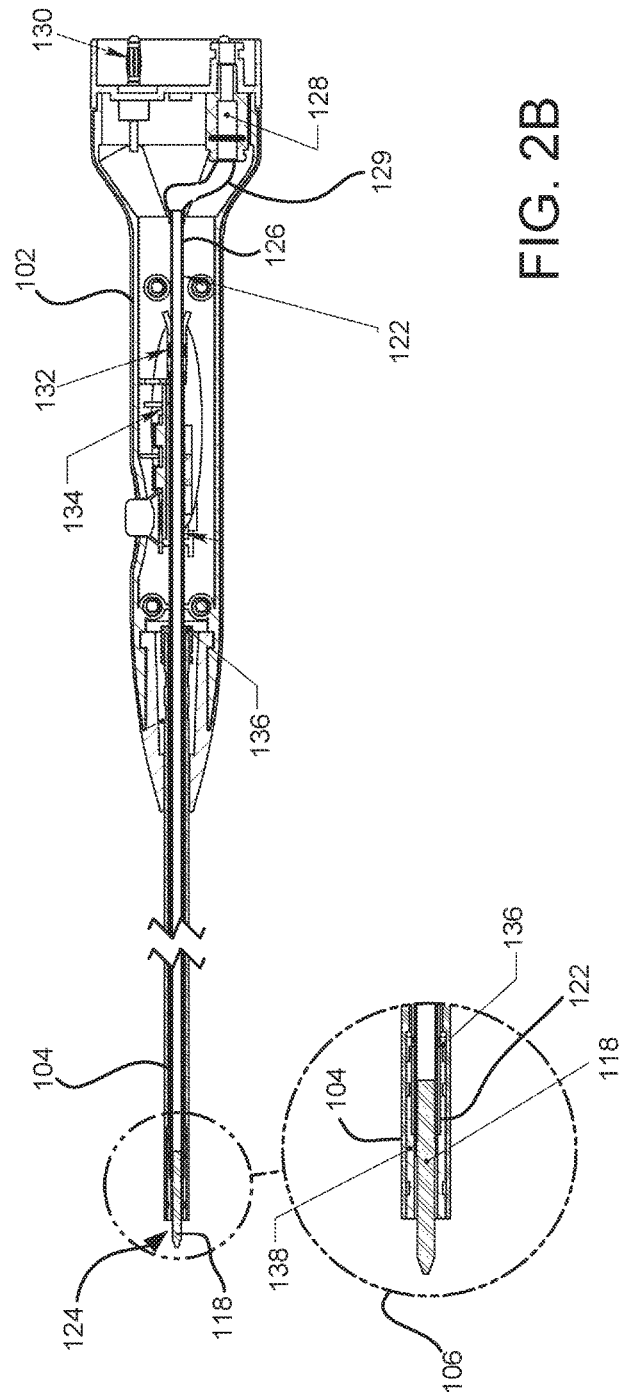
FIG. 2A
FIG. 2B

SKIN STATUS MONITOR AND METHOD THEREOF FOR ELECTROSURGICAL APPARATUSES

PRIORITY

This application claims priority to U.S. Provisional Patent Application No. 62/620,551, filed Jan. 23, 2018, entitled "SKIN STATUS MONITOR AND METHOD THEREOF FOR ELECTROSURGICAL APPARATUSES", the contents of which are hereby incorporated by reference in its entirety.

BACKGROUND

Field

The present disclosure relates generally to electrosurgery and electrosurgical systems and apparatuses, and more particularly, to a skin status monitoring apparatus for use with an electrosurgical apparatus in cold plasma applications.

Description of the Related Art

High frequency electrical energy has been widely used in surgery. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. In the latter example, the process can be relatively slow, generate large volumes of noxious smoke with vaporized and charred tissue, and may cause collateral damage to surrounding healthy tissue when high power electrosurgical energy is used. Precision accuracy can also be a problem, due to the width of the plasma beam.

SUMMARY

The present disclosure provides for a skin status monitoring apparatus that includes one or more sensors for sensing the applied energy density to an operative site in real time based on one or more monitored variables. The skin status monitoring apparatus of the present disclosure is coupled to a distal end of an electrosurgical device capable of generating cold plasma. Based on the sensed applied energy density, the applied power level of a cold plasma beam may be adjusted, such that, the applied energy density to the operative site remains within a beneficial range that achieves a desired physiological effect to the operative site.

In one aspect of the present disclosure, an electrosurgical apparatus is provided comprising: an applicator including a distal tip, the applicator configured for generating plasma and ejecting the generated plasma from the distal tip; and a standoff device including an applicator receiving portion, at least one post, and a base, the at least one post coupling the applicator receiving portion to the base and the applicator receiving portion configured to receive a distal portion of the applicator such that the distal tip of the applicator is disposed through an aperture of the applicator receiving portion at a predetermined fixed distance from a tissue surface when the base contacts the tissue surface.

According to one aspect of the electrosurgical apparatus, the base is configured in a ring shape having an aperture and the distal tip is oriented such that plasma is applied through the aperture of the base to the tissue surface.

According to one aspect of the electrosurgical apparatus, the base includes at least one sensor for monitoring at least one variable associated with the tissue surface when the base contacts the tissue surface.

According to one aspect of the electrosurgical apparatus, the electrosurgical further comprises at least one controller configured to determine the energy density applied to the tissue surface by the plasma based on the monitored at least one variable and adjust the applied power level of the plasma based on the determined energy density.

According to one aspect of the electrosurgical apparatus, the at least one controller is configured to adjust the applied power level of the plasma, such that, the applied energy density to the tissue surface remains within a predetermined beneficial range that achieves a desired physiological effect.

According to one aspect of the electrosurgical apparatus, the electrosurgical apparatus further comprises at least one controller configured to determine at least one of a direction and/or a speed of movement of the distal tip of the applicator relative to the tissue surface based on the at least one variable.

According to one aspect of the electrosurgical apparatus, at least one sensor is an annular sensor.

According to one aspect of the electrosurgical apparatus, the at least one sensor includes an array of sensors.

According to one aspect of the electrosurgical apparatus, the electrosurgical apparatus further comprises a circuit configured to serialize measurement data received from the array of sensors and output the measurement data via a single wire to the at least one controller.

According to one aspect of the electrosurgical apparatus, the at least one sensor is a temperature sensor and the at least one variable is the temperature of the tissue surface.

According to one aspect of the electrosurgical apparatus, the at least one sensor includes at least first and second contact electrodes.

According to one aspect of the electrosurgical apparatus, the electrosurgical apparatus further comprises a circuit including at least one controller, the circuit configured to apply a probe signal to the first and second contact electrodes and measure the voltage and current of the first and second contact electrodes, the at least one controller configured to determine tissue impedance based on the voltage and current measurements of the first and second contact electrodes and adjust the applied power level of the plasma based on the determined tissue impedance.

According to one aspect of the electrosurgical apparatus, the electrosurgical apparatus further comprising a circuit including at least one controller, the circuit configured to apply a probe signal to the first and second contact electrodes and measure the voltage and current of the first and second contact electrodes, the at least one controller configured to determine the phase shift between the voltage and current of the first and second contact electrodes and adjust the applied power level of the plasma based on the determined phase shift.

According to one aspect of the electrosurgical apparatus, the at least one sensor includes at least first and second acoustical transducers and the electrosurgical apparatus further comprises a circuit configured to apply an electrical oscillation to the first acoustical transducer, such that an acoustical emission is emitted from the first acoustical transducer into the tissue surface and received by the second acoustical transducer, the circuit further configured to determine an acoustical impedance of the tissue surface based on a distance between the first and second acoustical transducers and a time-of-flight for the acoustical emission emitted between the first and second acoustical transducers and adjust the applied power level of the plasma based on the determined acoustical impedance.

According to one aspect of the electrosurgical apparatus, the at least one sensor includes at least first and second acoustical transducers and the electrosurgical apparatus further comprises a circuit configured to apply an electrical oscillation to the first acoustical transducer, such that an acoustical emission is emitted from the first acoustical transducer into the tissue surface and received by the second acoustical transducer, the circuit further configured to determine an acoustical absorption of the tissue surface based on an amplitude of the acoustical signal received by the second acoustical transducer and adjust the applied power level of the plasma based on the determined acoustical impedance.

According to one aspect of the electrosurgical apparatus, the electrosurgical apparatus further comprises at least one sensor for determining electrical impedance of the plasma and at least one controller configured to adjust the applied power level of the plasma based on the determined electrical impedance.

According to one aspect of the electrosurgical apparatus, the electrosurgical apparatus further comprises a circuit for determining a change in phase shift between the voltage and current of the plasma and/or the tissue surface, the circuit including at least one controller configured to adjust the applied power level of the plasma based on the determined change in phase shift.

In another aspect of the present disclosure, an electrosurgical apparatus is provided comprising: an applicator including a distal tip, the applicator configured for generating plasma and ejecting the generated plasma from the distal tip and onto a tissue surface; an emission collector configured to collect emissions of a first type; and at least one controller configured to output a feedback signal to adjust the applied power level of the generated plasma based on the collected emissions.

According to one aspect of the electrosurgical apparatus, the feedback signal is provided to an electrosurgical generator coupled to the applicator.

According to one aspect of the electrosurgical apparatus, the emission collector is a sound tube and the first type of emissions are acoustical emissions from the plasma.

According to one aspect of the electrosurgical apparatus, the sound tube includes an open end for receiving the acoustical emissions, the open end being disposed proximately to the distal tip of the applicator.

According to one aspect of the electrosurgical apparatus, further comprises an acoustical transducer configured to receive the acoustical emissions via the sound tube and generate an electrical signal associated with a plasma acoustical emission frequency of the acoustical emissions and provide the electrical signal to the at least one controller.

According to one aspect of the electrosurgical apparatus, further comprises an amplifier for amplifying the electrical signal provided to the at least one controller and an analog-to-digital converter for digitizing the electrical signal provided to the at least one controller.

According to one aspect of the electrosurgical apparatus, the at least one controller, the amplifier, and the analog-to-digital converter are each co-located with the acoustical transducer.

According to one aspect of the electrosurgical apparatus, the emission collector is an optical fiber and the first type of emissions are optical spectra from the plasma.

According to one aspect of the electrosurgical apparatus, a tip of the optical fiber is disposed proximately to the distal tip of the applicator for collecting the optical spectra.

According to one aspect of the electrosurgical apparatus, further comprises an optical interface configured to receive the collected optical spectra and convert the optical spectra into electrical signals to be provided to the at least one controller.

According to one aspect of the electrosurgical apparatus, further comprises an optical interface configured to receive the collected optical spectra, the optical interface including a first bandpass filter and a first photodetector, the first bandpass filter configured to receive the collected optical spectra and pass at least one tissue-derived emission component of the optical spectra to the first photodetector, the first photodetector configured to convert the tissue-derived emission component to a first electrical signal and provide the first electrical signal to the at least one controller.

According to one aspect of the electrosurgical apparatus, the optical interface further includes a second bandpass filter and a second photodetector, the second bandpass filter configured to receive the collected optical spectra and pass at least one emission component associated with a carrier gas of the applicator to the second photodetector, the second photodetector configured to convert the at least one emission component associated with the carrier gas to a second electrical signal and provide the second electrical signal to the at least one controller.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is a schematic diagram of an electrosurgical apparatus in accordance with an embodiment of the present disclosure;

FIG. 2B is a cross sectional view of the electrosurgical apparatus shown in FIG. 2A taken along line A-A;

DETAILED DESCRIPTION

Figure 1:
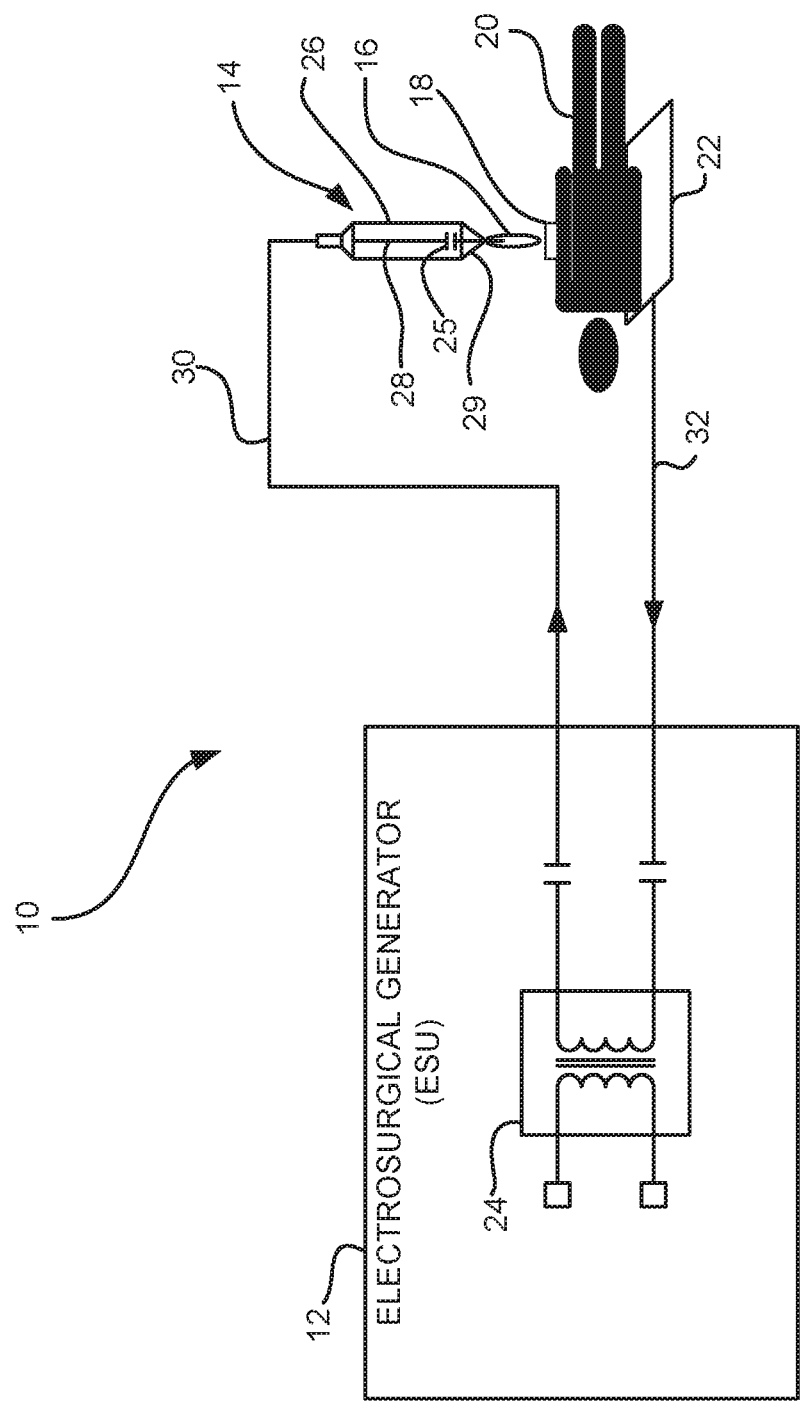
FIG. 1 is an illustration of an exemplary monopolar electrosurgical system in accordance with an embodiment of the present disclosure.

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

FIG. 1 shows an exemplary monopolar electrosurgical system generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20. Furthermore, a current limiting capacitor 25 is provided in series with the electrode 28 to limit the amount of current being delivery to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that transformer 24 may be disposed in the plasma generator handpiece 26, as will be described in various embodiments below. In this configuration, other transformers may be provided in the generator 12 for providing a proper voltage and current to the transformer in the handpiece, e.g., a step-down transformer, a step-up transformer or any combination thereof.

Referring to FIG. 2A, an electrosurgical apparatus 100 in accordance with the present disclosure is illustrated. Generally, the apparatus 100 includes a housing 102 having a proximal end 103 and a distal end 105 and a tube 104 having an open distal end 106 and a proximal end 108 coupled to the distal end 105 of the housing 102. The housing 102 includes a right side housing 110 and left side housing 112, and further includes provisions for a button 114 and slider 116. Activation of the slider 116 will expose a blade 118 at the open distal end 106 of the tube 104. Activation of the button 114 will apply electrosurgical energy to the blade 118 and, in certain embodiments, enable gas flow through the flow tube 122, as will be described in detail below.

Additionally, a transformer 120 is provided on the proximal end 103 of the housing for coupling a source of radio frequency (RF) energy to the apparatus 100. By providing the transformer 120 in the apparatus 100 (as opposed to locating the transformer in the electrosurgical generator), power for the apparatus 100 develops from higher voltage and lower current than that required when the transformer is located remotely in the generator, which results in lower thermalization effects. In contrast, a transformer back in the generator produces applicator power at a lower voltage, higher current with greater thermalization effects. Therefore, by providing the transformer 120 in apparatus 100, collateral damage to tissue at the operative site is minimized.

A cross section view along line A-A of the apparatus 102 is shown in FIG. 2B. Disposed within the housing 102 and tube 104 is flow tube 122 which runs along the longitudinal axis of the apparatus 100. On a distal end 124 of the flow tube 122, the blade 118 is retained within the flow tube 122. A proximal end 126 of the flow tube 122 is coupled to a source of gas via a tube connector 128 and flexible tubing 129. The proximal end 126 of the flow tube 122 is also coupled to a source of RF energy via plug 130 which couples to transformer 120. The flow tube 122 is made of an electrically conducting material, preferably stainless steel, as to conduct the RF energy to the blade 118 when being employed for plasma applications or electrosurgical cutting as will be described below. The outer tube 104 is constructed from non-conductive material, e.g., Lestran. The slider 116 is coupled to the flow tube 122 via a retaining collar 132. A printed circuit board (PCB) 134 is disposed in the housing 102 and controls the application of the RF energy from the transformer 120 via the button 114.

It is to be appreciated that the slider 116 may be freely moveable in a linear direction or may include a mechanism for incremental movements, e.g., a ratchet movement, to prevent an operator of the apparatus 100 from over extending the blade 118. By employing a mechanism for incremental movements of the blade 118, the operator will have greater control over the length of the exposed blade 118 to avoid damage to tissue at the surgical site.

An enlarged view of the distal end 106 of the outer tube 104 is also illustrated in FIG. 2B. Here, the blade 118 is coupled to the flow tube 122 which is held in place in the outer tube 104 by at least one seal 136. The at least one seal 136 prevents backflow of gas into tube 104 and housing 102. A cylindrical ceramic insert 138 is disposed in the distal end of the outer tube 104 to maintain the blade along the longitudinal axis of the apparatus 100 and provide structural support during mechanical cutting when the blade is exposed beyond the distal end of the outer tube 104.

Figures 3A, 3B:
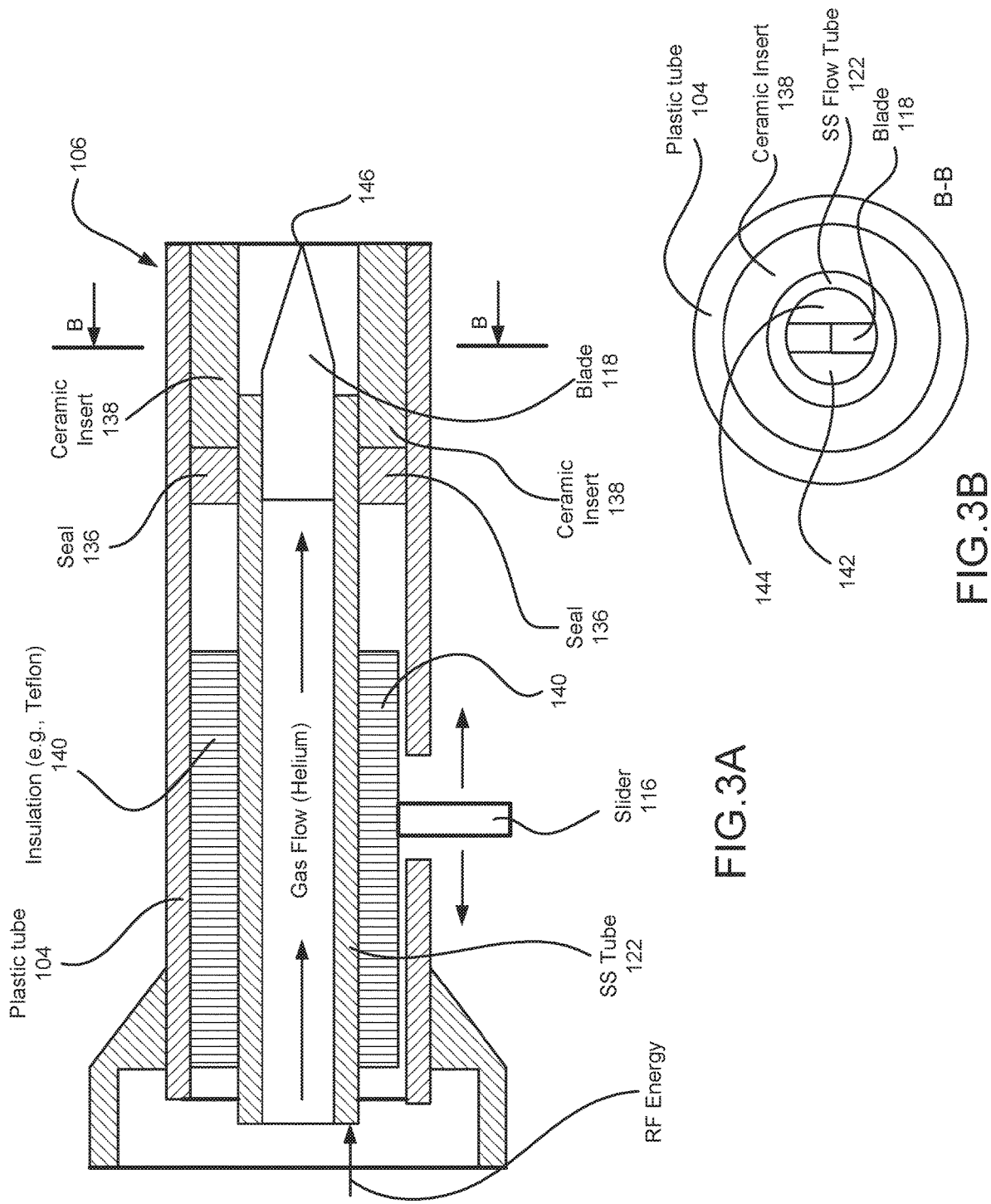
FIG. 3A is an enlarged cross sectional view of the electrosurgical apparatus in accordance with an embodiment of the present disclosure.
FIG. 3B illustrates a front view of the electrosurgical apparatus shown in FIG. 3A taken along line B-B.

The operational aspect of the apparatus 100 will now be described in relation to FIGS. 3A and 3B, where FIG. 3A shows an enlarged cross section of the apparatus and FIG. 3B illustrates a front view of the apparatus.

Referring to FIG. 3A, the flow tube 122 is disposed in the outer tube 104 with a cylindrical insulator 140 disposed around the flow tube 122. Slider 116 is coupled to the insulator 140 and is employed to extend and retract the blade 118. At the distal end 106 of the outer tube 104, the annular or ring shaped seal 136 and cylindrical ceramic insert 138 are disposed about the flow tube 122. As can be seen In FIG. 3B, the generally planar blade 118 is coupled to an inner circumference of the cylindrical flow tube 122 such that two gas passageways 142, 144 are formed on the both sides of the blade 118. As gas flows from the proximal end 103 of the housing through the flow tube 122, the gas will pass over the blade 118 out the distal end of the outer tube 104.

When the blade is in the retracted position as shown in FIG. 3A, the apparatus 102 is suitable for generating plasma. In the retracted position, RF energy is conducted to a tip 146 of the blade 118 from an electrosurgical generator (not shown) via the flow tube 122. An inert gas, such as helium or argon, is then supplied to the flow tube from either the electrosurgical generator or an external gas source. As the inert gas flows over the sharp point 146 of the blade 118 held high voltage and high frequency, a cold plasma beam is generated.

Figure 4:
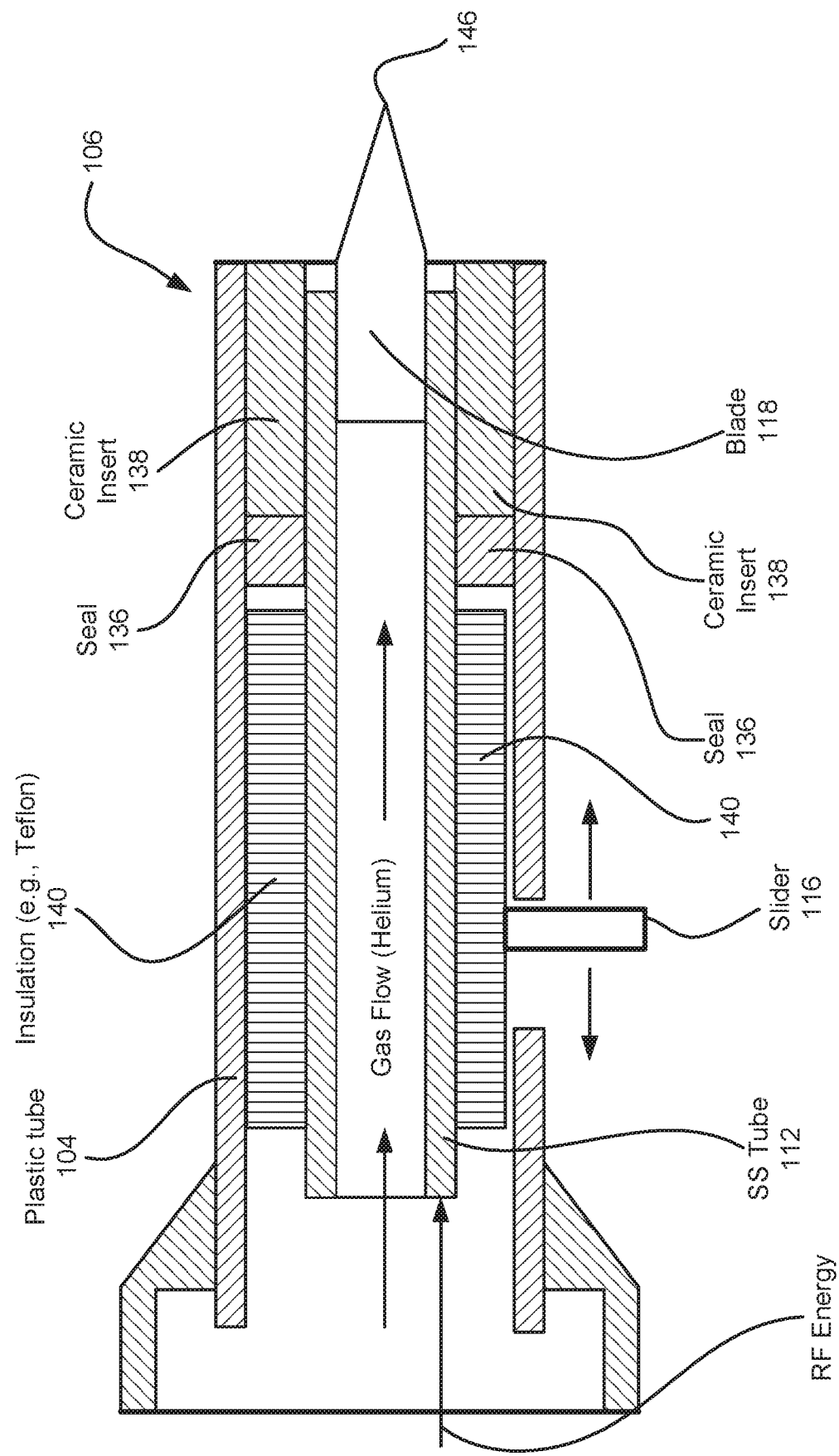
FIG. 4 is an enlarged cross sectional view of the electrosurgical apparatus shown in FIG. 3A with a blade extended.

Referring to FIG. 4, the blade 118 is advanced, via slider 116, so the tip 146 is extended pass the distal end 106 of the outer tube 104. In this state, the blade 118 can be used for two cutting modes: mechanical cutting and electrosurgical cutting. In the mechanical cutting mode, RF or electrosurgical energy is not applied to the flow tube 122 or blade 118, and therefore, the blade 118 is in a de-energized state. In this mode, the blade 118 can be used excise tissue via mechanical cutting. After the tissue is removed, the blade 118 may be retracted via the slider 116 and electrosurgical energy and gas may be applied via button 114 to generate a cold plasma beam for cauterization, sterilization and/or hemostasis of the operative patient site.

In the electrosurgical cutting mode, the blade 118 is advanced and used while both electrically energized and with inert gas flow. This configuration resembles an electrosurgical knife approach, where the electrosurgical energy does the cutting. However, with the addition of the inert gas flow, cuts made show virtually no eschar, with very little collateral damage along the side walls of the cut. The cutting speed is considerably faster, with less mechanical cutting resistance as compared to when the knife blade is not electrically energized, i.e., the mechanical cutting mode. Hemostasis is also affected during this process.

As described above, electrosurgical devices capable of generating cold plasma, such as, plasma generator generally 14 and apparatus 100 may be used in electrosurgical procedures to apply electrosurgical energy via a generated cold plasma beam to an operative site (e.g., the tissue of a patient). As will be described below, the energy density applied to an operative site may vary (significantly) based on any one of a plurality of factors. However, it is critical that the energy density applied to an operative site remain within a certain narrow beneficial range to achieve the desired physiological effect to the operative site. The present disclosure provides for a skin status monitoring apparatus that is configured to sense the applied energy density to an operative site in real time based on one or more factors. Based on the sensed applied energy density, the applied power level of the cold plasma beam may be adjusted, such that, the applied energy density to the operative site remains within the beneficial range that achieves the desired physiological effect to the operative site. In one embodiment, the skin status monitoring apparatus of the present disclosure is configured to be coupled to a distal end of an electrosurgical device capable of generating cold plasma. In other embodiments, an electrosurgical apparatus may include integrated skin status monitoring components.

Various surgical procedures can be affected by the deposition of energy to an operative site, for example, by using a cold plasma generating device, such as, but not limited to, apparatuses 14 and 100, described above. More specifically, a given minimum energy density (e.g., in Joules per unit area) must be applied to an operative site to achieve the desired physiological effect. However, there may be a threshold energy density beyond which tissue damaging effects will occur to the operative site. In some cases, the threshold between beneficial and damaging effects may be quite steep, and a relatively small increase in energy density can cross that threshold. In other words, an increase of only a few percent of applied energy density can make the difference between a therapeutic effect and a damaging one.

Several factors influence the applied energy density to an operative site. These include, but are not limited to, the application area, the applied power level of the plasma beam, the ability of the application site to absorb the energy, any cooling factors which remove energy from the application site, and the dwell time. In the case of a cold plasma jet applicator, such as apparatus 14 and 100 described above, the flow rate of carrier gas, which acts as an additional coolant, also affects the net applied energy density to the operative site.

Cold plasma is applied from an applicator tip (e.g., such as, via distal end 106 and flow tube 122 of apparatus 100) of a cold plasma generating device to an application site. The distance from the applicator tip to the application site can play a significant role in applied energy density. This is especially true for optical-based energy applicators, such as lasers. Here, the applied power density scales as the inverse square of the applicator distance from the application site, and relatively small changes in applicator distance can have significant effects in applied power density. It should be noted that the term applied power density refers to the instantaneous amount of effective power being applied to a given area, given in units of power per unit area, for example, Watts/cm$^2$. Applied energy density is determined by the applied power density multiplied by the duration that power density is applied to the given area. This duration is sometimes referred to as the dwell time. The units of applied energy density are in energy per unit area, such as Watt-seconds/cm$^2$ or Joules/cm$^2$. It should be noted that the term "applied" or "effective" is intended to denote the actual power density or energy density absorbed at the operative site and takes into account various mechanisms that may remove power or energy such as cooling by gas flow, blood flow, and/or evaporative cooling.

Many procedures require the applicator beam (i.e., the cold plasma beam ejected from the applicator tip of the cold plasma generating device) to be scanned over a given area of an operative site. The dwell time is then related to the scanning speed of the applicator tip over the operative site. The faster the scanning speed, the lower the dwell time, and vice-versa. Since the applied energy density is the product of the applied power density and the dwell time, all other factors being equal, the faster the scanning speed, the lower the applied energy density to the operative site, and so on.

Of the factors that affect the applied energy density, the scanning speed is the least easily controlled, particularly when the applicator is being scanned by hand, as is the case with apparatus 14 and 100 described above. In situations where the threshold between beneficial and damaging applied energy density is relatively narrow, a relatively small change in applicator scanning speed can cross that threshold, producing undesirable physiological effects to the operative site.

In accordance with an embodiment of the present disclosure, methods and apparatuses are provided for monitoring the applied energy density to an operative site in real time, so that variations in the factors that affect this energy density can be compensated for, producing a uniform physiological effect over a given area. For example, the applied power level may be adjusted in response to a variable monitored in real-time by an apparatus of the present disclosure at the application site. If the monitored variable indicates that the applied energy density is approaching a predetermined damage threshold, the applied power level of the cold plasma beam generated by the applicator could be proportionately reduced to maintain the applied energy density within a predetermined beneficial range. Similarly, if it is determined by the apparatus of the present disclosure that the applied energy density has fallen below the predetermined beneficial level or range, the applied power level of the cold plasma beam generated by the applicator could be proportionately increased to maintain the applied energy density within a predetermined beneficial range. In the case of compensating for variable scanning speed, if the apparatus of the present disclosure determines the applicator is momentarily moving too slowly, the applied power level would be reduced, and the applied power level would be increased if the apparatus of the present disclosure determines applicator is moving too fast. It is to be appreciated that the apparatus of the present disclosure will be described in greater detail below.

Several variables may potentially be monitored that indicate the applied energy density. These include tissue surface temperature, tissue electrical impedance, and acoustical characteristics. However, some of these monitored variables may be interfered with by the energy application process. For example, the process of measuring tissue electrical impedance typically utilizes a test signal whose magnitude is on the order of several millivolts, while the voltages employed by a cold plasma jet can be on the order of several kilovolts. Fortunately, such cold plasma jets are electrically pulsed and the quiet, inter-pulse period may be used for electrical impedance measurements. A similar argument could be made for acoustic monitoring, such as using ultrasonic characteristics, where the inter-pulse period may be used for acoustic measurements. Temperature measurement may be achieved by direct tissue surface contact, or by using infra-red emissions. In the latter case, again, the contribution from the energy application must be filtered out or otherwise removed. It is to be appreciated that the skin status monitoring apparatus of the present disclosure (first shown in FIG. 8) may be configured to monitor any one of the variables described above using these techniques to filter out any interference by the electrosurgical applicator to the measurements of the variable being monitored.

Figure 5A:
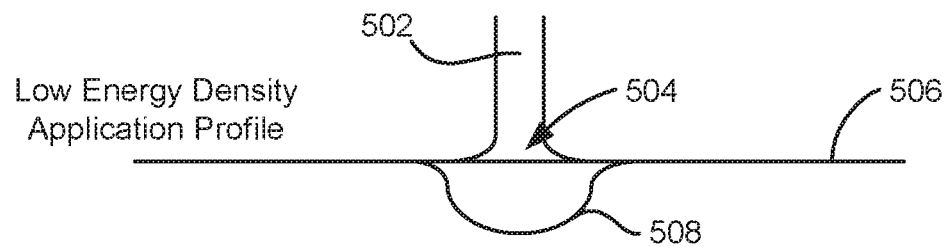
FIG. 5A illustrates a tissue thermal spread profile produced on an operative site by a plasma beam of low energy density profile in accordance with an embodiment of the present disclosure.

For a given applied energy density and tissue characteristics, a temperature profile is produced both in the depth of the tissue and laterally across the surface of the tissue and away from the point of application. For example, referring to FIGS. 5A-5C, various applied energy density profiles and their relative effects on the thermal or temperature spread profile produced on the tissue of an operative site are shown in accordance with the present disclosure. In FIG. 5A, a plasma beam or jet 502 of low energy density is applied by an applicator (such as, apparatuses 14, 100, described above) to a point of application 504 on the tissue surface 506 of a patient. The applied energy density to the tissue surface 506 by the plasma beam 502 produces a tissue thermal spread profile 508 spreading radially from the point of application 504 into the depth of the patient's tissue and laterally across the tissue surface 506 away from the point of application 504.

Figure 5B:
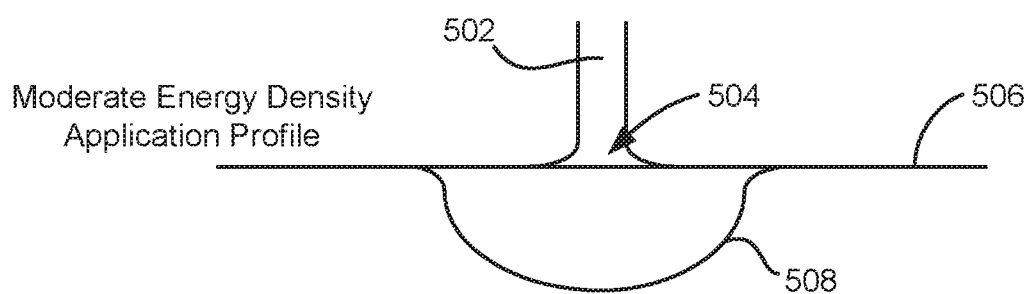
FIG. 5B illustrates a tissue thermal spread profile produced on an operative site by a plasma beam of medium energy density profile in accordance with an embodiment of the present disclosure.
Figure 5C:
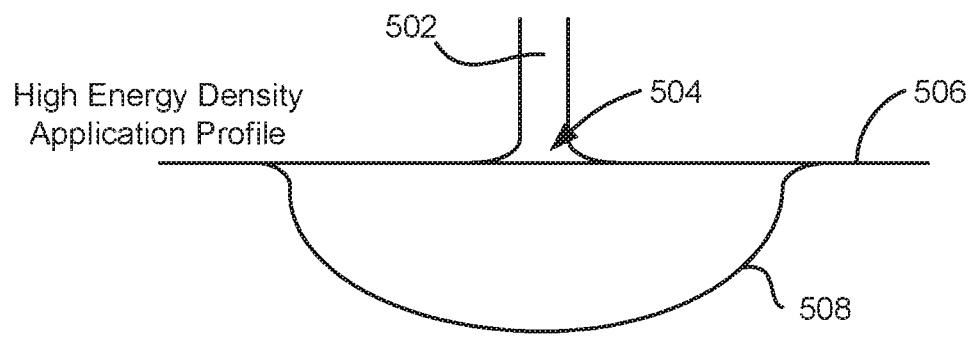
FIG. 5C illustrates a tissue thermal spread profile produced on an operative site by a plasma beam of high energy density profile in accordance with an embodiment of the present disclosure.

In FIG. 5B, a moderate energy density (i.e., higher than the low energy density applied in FIG. 5A) is applied to the tissue surface 506 of the patient and, in FIG. 5C, a high energy density (i.e., higher than the moderate energy density applied in FIG. B) is applied to the tissue surface 506 of the patient. As can be seen by examination of FIGS. 5A-5C, as the energy density applied to point 504 of tissue surface 506 is increased, the tissue thermal spread profile 508 spreads further away from point 504 both laterally across tissue surface 506 and in the depth of tissue penetration. In this way, by measuring certain characteristics of the thermal spread profile 508 produced by the application of plasma beam 502 to point 504 of tissue surface 506, the applied energy density profile may be determined.

Figure 6:
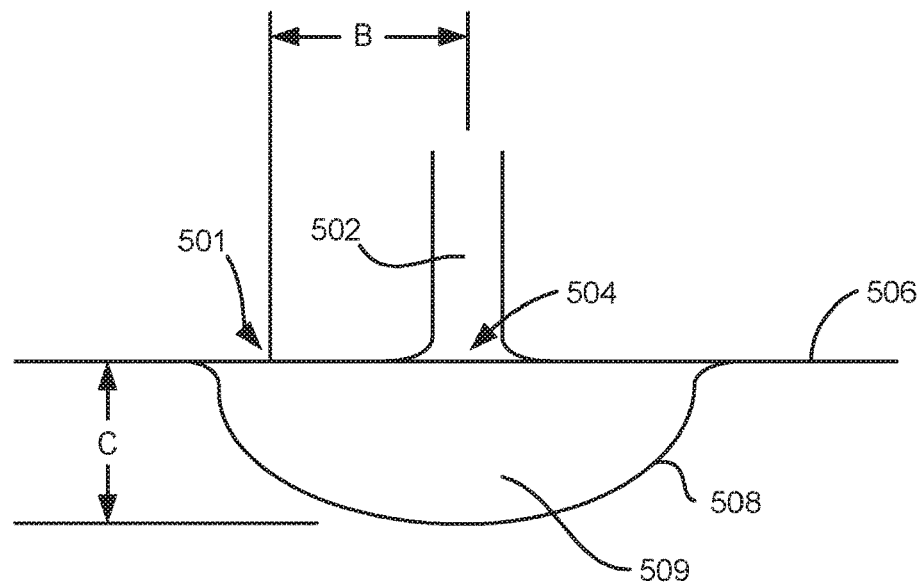
FIG. 6 is another illustration of a tissue thermal spread profile produced on an operative site by a plasma beam in accordance with an embodiment of the present disclosure.

For example, referring to FIG. 6, the temperature at a fixed distance B from the point of application 504 to a point 501 on tissue surface 506 laterally disposed from point 504, may be measured and used to determine the applied energy density as well as the depth of the thermally affected zone 509 into the tissue. With applied energy density at point 504, a measured temperature at point 501 can be used to both determine the energy density at point 504 and the depth C of penetration of the thermally affected zone 509. In principle, the applied energy density can be calculated based on the measured surface temperature a given distance away from the point of application. However, the values of variables such as thermal conductivity, specific heat, and loss mechanisms including conduction, evaporation and radiative loss may only be approximately known, and their values may also be temperature dependent. In practice, the relationship between applied energy density and surface temperature can be determined experimentally and then stored in a look-up table.

In certain applications, such as skin resurfacing and wrinkle removal, it is important to limit the depth C of the thermally affected zone 509 (i.e., the volume of tissue defined by the thermal spread profile 508). Underlying vascularization must not be damaged in the energy deposition process.

Figure 7A:
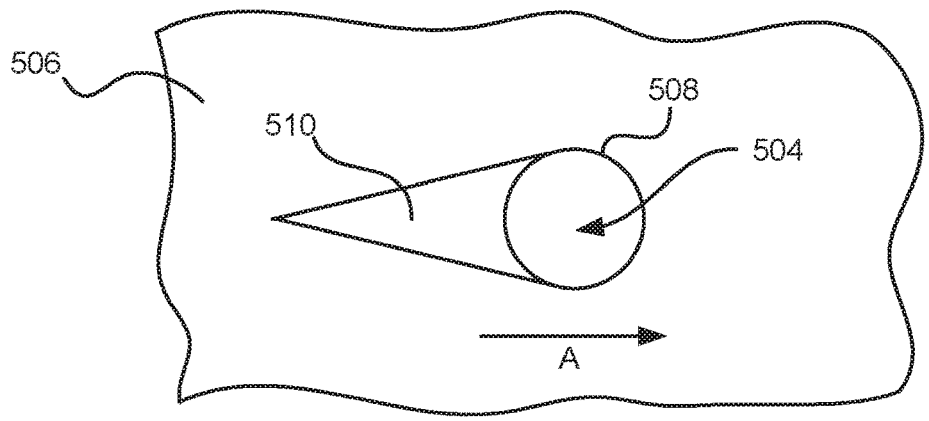
FIGS. 7A and 7B illustrate a trialing tail of thermal dissipation formed by a scanning motion of an electrosurgical apparatus in accordance with an embodiment of the present disclosure.

An additional complication in surface temperature measurement is that the radial symmetry of temperature profile 508 can be affected by the scanning motion of the applicator. This effect is illustrated in FIG. 7A in accordance with the present disclosure. When the tip of the applicator is moved in a direction A (indicated in FIG. 7A) across the tissue surface 506 of a patient, a trialing "tail" 510 of thermal dissipation may be formed in the temperature profile 508. A temperature measurement in the thermal dissipation tail 510 of the point of energy application 504 will contain contributions from both the usual radial surface thermal spread 508 as well as a contribution from the dissipation of the energy deposition itself.

Figure 8A:
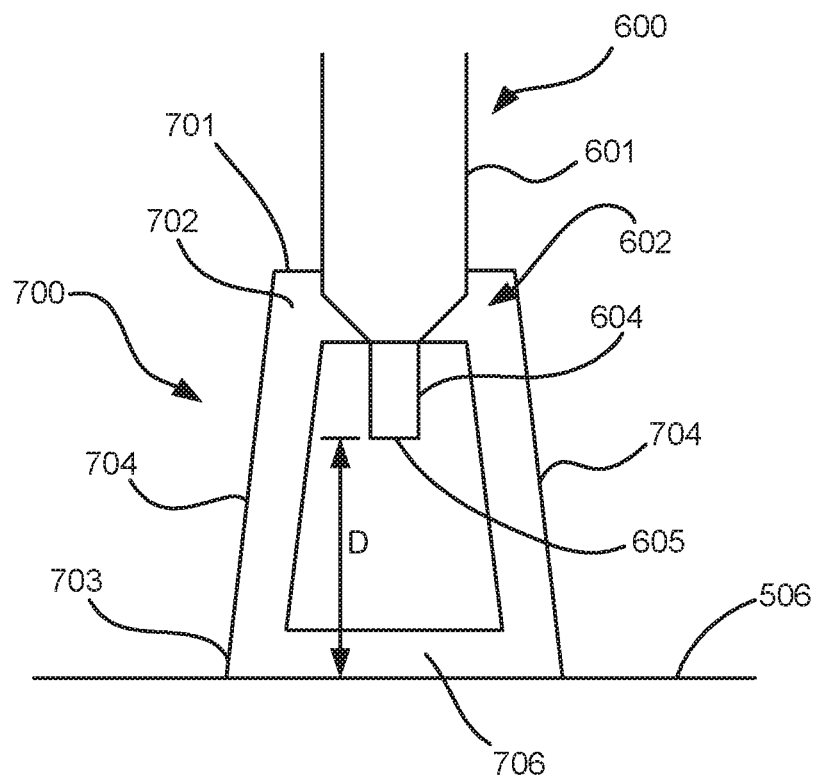
FIG. 8A is a side view of a skin status monitoring apparatus coupled to a distal end of an electrosurgical apparatus in accordance with an embodiment of the present disclosure.
Figure 8B:
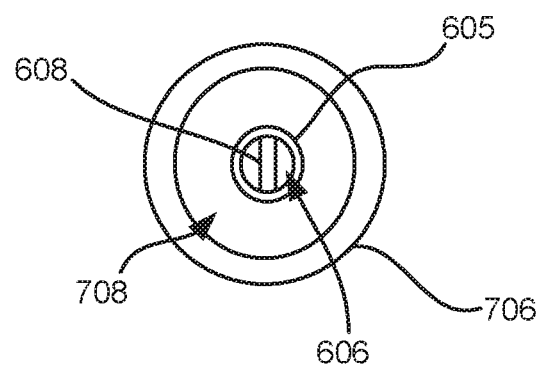
FIG. 8B is a view through a distal end of the skin status monitoring apparatus of FIG. 8A in accordance with an embodiment of the present disclosure.
Figure 9:
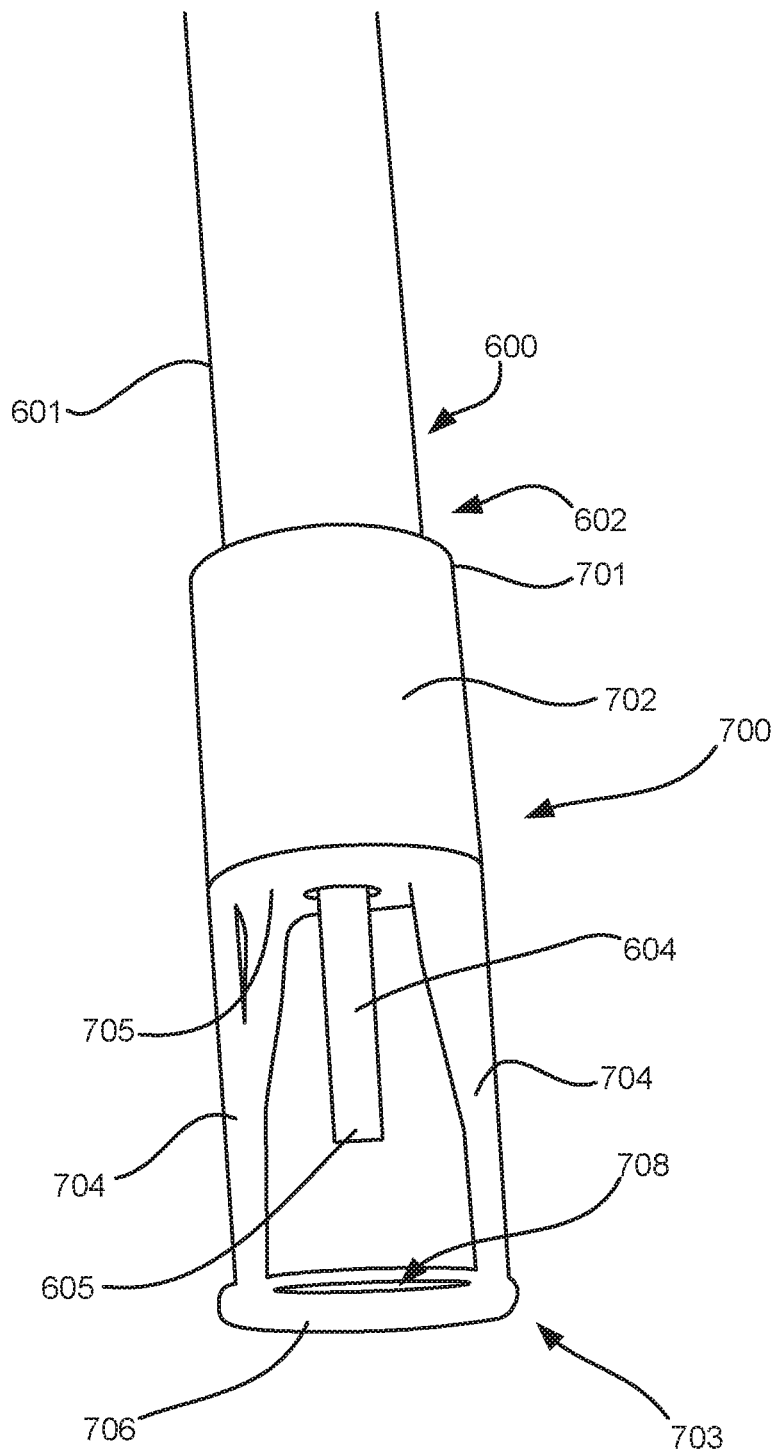
FIG. 9 is a perspective view of the skin status monitoring apparatus of FIG. 8A in accordance with an embodiment of the present disclosure.

One of the variables that affects the applied energy density, applicator distance to the tissue surface, can be controlled and fixed by use of a standoff device 700, illustrated in FIGS. 8A, 8B, and 9 in accordance with the present disclosure. It is to be appreciated that, as will be described below, standoff device 700 may be used as the skin status monitoring apparatus described above.

As shown in FIGS. 8A, 8B, and 9, standoff 700 may be coupled to a distal portion 602 of an applicator 600. It is to be appreciated that applicator 600 may represent any of apparatuses 14, 100, described above, or any other electrosurgical apparatus capable of applying cold plasma to an operative site. Applicator 600 includes a handle housing 601 and a distal applicator tip or nozzle 604, which extends distally from the housing 601. Although not shown, in one embodiment, a shaft or tube couples housing 601 to distal tip 604. Cold plasma produced by applicator 600 is ejected from an aperture 606 (shown in FIG. 8B) disposed on the distal end 605 of tip 604 and applied to the tissue surface 506 of a patient. It is to be appreciated that an electrode 608 may be disposed within the interior of tip 604 to ionize carrier gas provided to tip 604 to create a cold plasma beam. In one embodiment, the electrode 608 may be retractable and configured as a planar blade in a similar manner to blade 118 of apparatus 100 described above. In other embodiments, electrode 608 may be configured in other suitable shapes, e.g., a needle, ball, wire, or any other type of electrode without deviating from the scope of the present disclosure.

Standoff 700 includes an applicator receiving portion 702 disposed toward a proximal end 701 of standoff 700 and a base 706 disposed toward a distal end 703 of standoff 700. Base 706 is coupled to applicator receiving portion 702 via one or more supports or posts 704 coupling to an outer circumference of base 706. As best seen in FIG. 9, receiving portion 702 is configured to receive a distal portion 602 of applicator 600 (e.g., in a channel or slot extending from end 701 to surface 705), such that, applicator tip 604 is disposed through an aperture of surface 705 of standoff 700. The distal portion 602 may include a distal portion of housing 601, a distal portion of a shaft or tube coupling housing 601 to tip 604, and/or a portion of tip 604. In one embodiment, standoff 700 may include a securing means (e.g., a clamp or other securing means disposed on end 701) for securing standoff 700 to tip 604 and/or distal portion 602 when distal portion 602 of applicator 600 is received by receiving portion 702. In one embodiment, base 706 is configured in a ring or annular shape, such that, base 706 includes an aperture 708 defined by an outer circumference. As best seen, in FIG. 8B, when standoff 700 is coupled to the distal portion 602 of applicator 600, aperture 606 of tip 604 and aperture 708 of base 706 are coaxially aligned, such that, when plasma exits aperture 606 of tip 604, the plasma is directed to aperture 708.

As shown in FIG. 8A, base 706 is disposed away from receiving portion 702 via posts 704, such that, when base 706 comes into contact with tissue surface 506, the distal end 605 of tip 604 is held at a fixed predetermined distance D from base 706/tissue surface 506. In this way, the effect that the distance D from the distal end 605 of tip 604 to the tissue surface 506 has on the applied energy density is held constant. While the distance D from the distal end 605 of tip 604 is held constant, the applied energy density is more easily held constant and the remaining factors effecting applied energy density may be focused on, as will be described below.

Figure 10A:
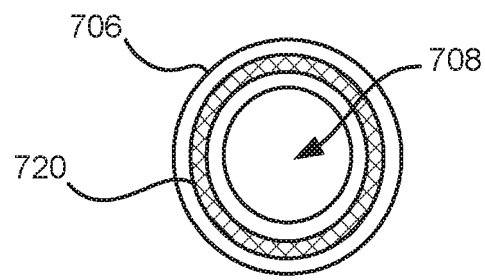
FIG. 10A illustrates the skin status monitoring apparatus of FIG. 8A including a ring sensor in accordance with an embodiment of the present disclosure.
Figure 10B:
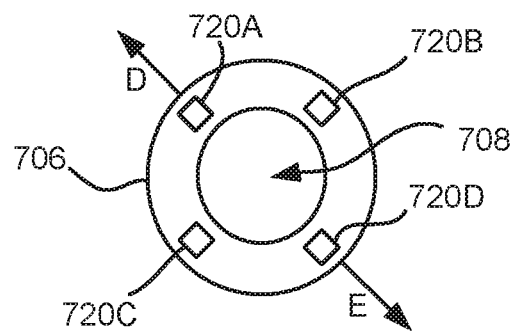
FIG. 10B illustrates the skin status monitoring apparatus of FIG. 8A including a plurality of individual sensors in accordance with an embodiment of the present disclosure.

The standoff support base 706 (FIG. 8B) provides a convenient location for sensor monitoring of the tissue status during energy application. In one embodiment, base 706 includes one or more embedded sensors for monitoring various characteristics or properties of the tissue surface 506 (e.g., temperature) of the operative site. When base 706 comes into contact with tissue surface 506 during an electrosurgical procedure, the sensors in base 706 will also contact the tissue surface 506 to obtain desired measurements (e.g., in one embodiment, temperature measurements). For example, each of FIGS. 10A and 10B include views through a distal end 703 of standoff 700 with various sensor configurations implemented with base 706 in accordance with the present disclosure. In FIG. 10A, a ring or annular sensor 720 (e.g., temperature sensor) is shown embedded in base 706, and, in FIG. 10B, one or more discrete or individual sensors 720 (i.e., 720A-D) are shown embedded in base 706. As will be described in greater detail below, each sensor 720 may be coupled to one or more components of standoff 700 and/or applicator 600 (e.g., a controller or processor), where any measurements obtained by sensors 720 may be provided.

From the standpoint of cost and complexity, it would be desirable to use the lowest number of sensors 720 possible to achieve the necessary feedback of applicator power level. However, in consideration of the potential effects of the thermal dissipation "tail" 510 of a scanned applicator (shown in FIG. 7A), a single temperature sensor must be radially symmetric to account for the possibility that the applicator can be moved in any direction. As shown in FIG. 10A, a ring sensor 720 includes the requisite radially symmetric shape. Alternately, referring to FIG. 10B, an array of at least two temperature sensors 720 may be utilized. It is to be appreciated that any given temperature sensor 720 must have low thermal mass so that the sensor 720 can respond quickly to any temperature changes measured on tissue surface 506 and use those measurements in a feedback loop to adjust the applied power level of the plasma beam 502 in a timely manner.

The use of multiple sensors 720, as shown in the embodiment of FIG. 10 ft permits the detection of applicator motion direction as at least one or more sensors 720 will be in the downstream thermal dissipation "tail" 510 created by the motion of applicator 600. The measurements obtained by the sensor(s) 720 in the downstream thermal dissipation "tail" 510 will have a higher temperature relative to the other measurements obtained by the remaining sensors(s) 720 disposed at the point of application 504. In this way, the higher temperature measured by the sensor(s) 720 in the dissipation "tail" 510 may be used to determine the direction of "tail" 510. Once the direction of "tail" 510 is obtained, the direction of the motion of the applicator 600 may also be determined, as it will be in the opposite direction of the direction of "tail" 510. For example, if the temperature sensed by temperature sensor 720A is higher than the temperature sensed by temperature sensors 720B-D, it may be determined that "tail" 510 is oriented in a direction D away from sensor 720A and along surface 506 and that the motion of applicator 600 is in a direction E (opposite D) along surface 506.

Figure 7B:
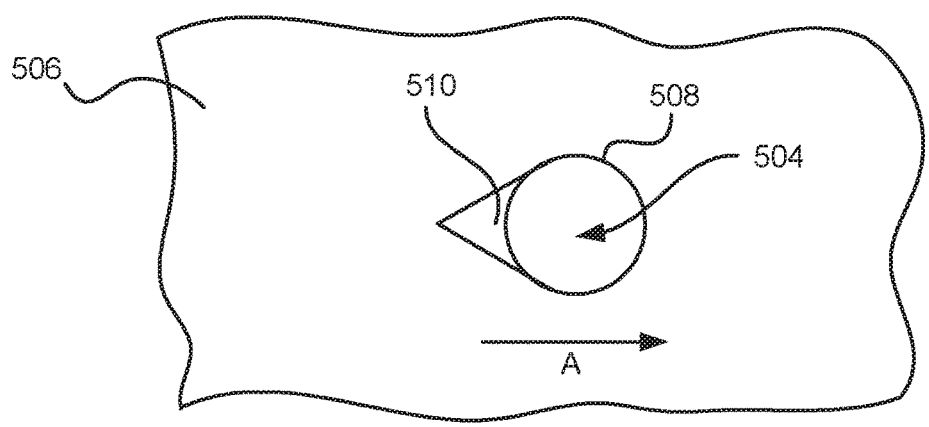

The degree of asymmetry between the upstream temperature and the downstream temperature (i.e., 510 in FIG. 7A) for a given power setting may be used to infer the speed of the applicator. For example, if the applicator is moved relatively slowly, for a given power setting, the applied energy density will be high, so the time required to dissipate that energy will be longer. As a result, the asymmetry will be larger producing a longer "tail" 510 as shown in FIG. 7A. By comparison, if the applicator 600 is moved more quickly, the applied energy density will be lower, and the "tail" 510 will be shorter as shown in FIG. 7B.

Figure 11A:
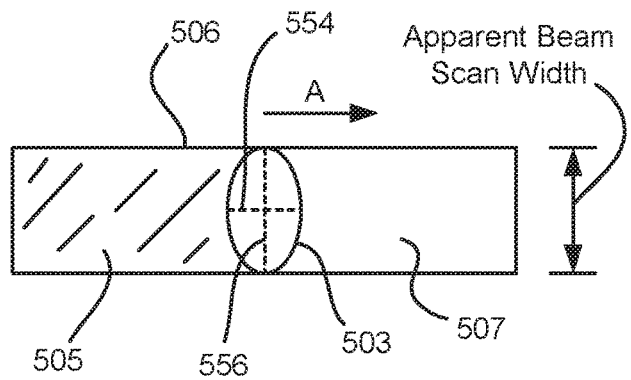
FIG. 11A illustrates a plasma beam scan produced by an electrosurgical apparatus with a blade-type electrode in accordance with an embodiment of the present disclosure.
Figure 11B:
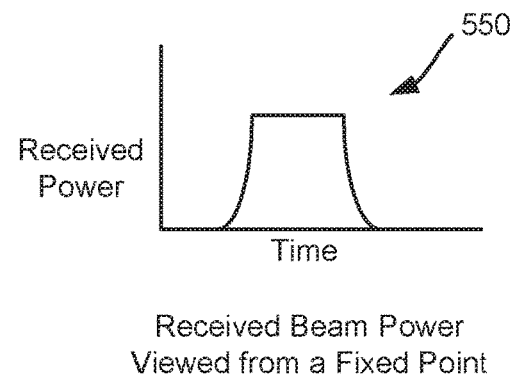
FIG. 11B is a graph corresponding to FIG. 11A of received plasma beam power viewed from a fixed point in accordance with an embodiment of the present disclosure.
Figure 11C:
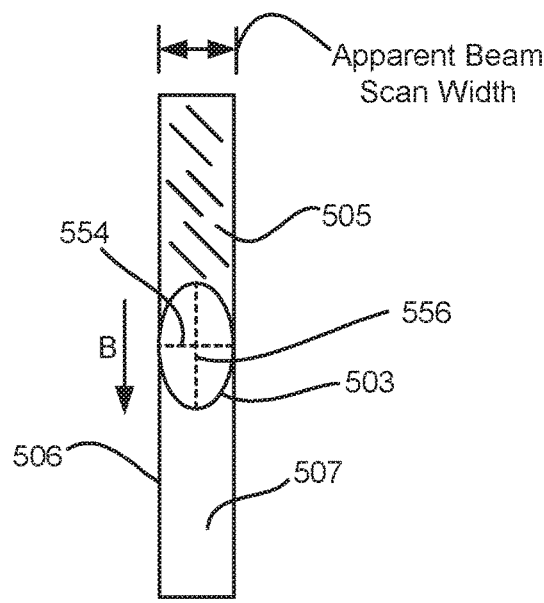
FIG. 11C is another illustration of a plasma beam scan produced by an electrosurgical apparatus with a blade-type electrode in accordance with an embodiment of the present disclosure.
Figure 11D:
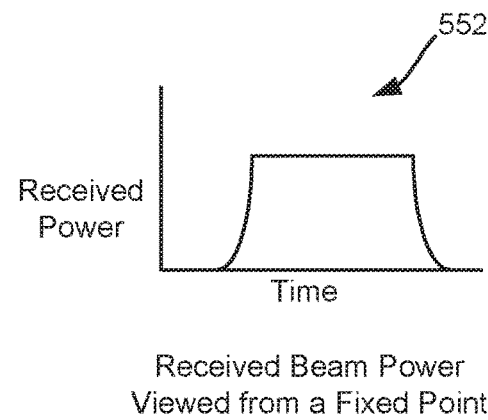
FIG. 11D is a graph corresponding to FIG. 11C of received plasma beam power viewed from a fixed point in accordance with an embodiment of the present disclosure.

The inclusion of multiple individual sensors 720 also permits potential compensation for an asymmetric energy application profile. In the case of a cold plasma jet applicator 600, the applicator electrode 608 may be in the form of a blade (as described above) which is wider than it is thick. This gives rise to an elliptical energy application profile. For example, referring to FIG. 11A, the beam footprint 503 of plasma beam 502 produced on tissue surface 506 by the plasma beam 502 generated by an applicator 600 including a planar blade-shaped electrode 608 is shown in accordance with the present disclosure. The applicator 600 is being moved such that the beam 502 is scanning tissue surface 506 in a direction A. As beam 502 scans tissue surface 506, along the path scanned by beam 502 there is treated tissue 505, where beam 502 has already scanned over, and untreated tissue 507, where beam 502 has yet to pass over, but will pass over if beam footprint 503 continues to move in the same direction. If the applicator 600 is scanned in a direction A along the minor ellipse axis 554 of beam footprint 503, as shown in FIG. 11A, the energy is scanned over a larger area. In addition, the instantaneous dwell time, as seen from a given point on the target tissue as the beam 502 is scanned over it (i.e., indicated by footprint 503) will be shorter, as indicted in graph 550 shown in FIG. 11B. This is due to the fact that in the direction of movement A, the length of the axis aligned with the direction of movement A (i.e., the minor ellipse axis 554) is minimized. The wider path and shorter dwell time produced from the minor ellipse axis 554 aligning with the direction of movement A of applicator 600 combine to reduce the overall applied energy density.

Conversely, if the applicator 600 is scanned in a direction B along the major ellipse axis 556, as shown in FIG. 11 B, the energy is spread over a narrower path (relative to the path generated when scanned over the minor ellipse axis 554, as shown in FIG. 11A). The instantaneous dwell time in this scenario, as indicated in graph 552 in FIG. 11D, is longer due to the fact that in the direction of movement B, the length of the axis aligned with the direction of movement B (i.e., the major ellipse axis 556) is maximized. The narrower path and longer dwell time produced from the major ellipse axis 556 aligning with the direction of movement B of applicator 600 results in a higher applied energy density, even though the applied power level and scan speed is the same in each of the scenarios depicted in FIGS. 11A and 11B. Multiple sensors 720 included in base 706 of standoff 700 allow for the detection of these two orientations, or orientations between them, and adjustment of the applied power level for a constant applied energy density.

Consider an example of a beam footprint ellipse with a minor axis of 1 mm and a major axis of 2 mm. Individual sensor spacing would have to be sufficiently close to be able to reliably detect the difference of these two axes. A sensor spacing of at least 0.5 mm would be sufficient in this example. Scanning along the minor axis would produce a temperature rise indication over a greater number of sensors, since the beam is wider, than scanning along the minor axis. Furthermore, scanning along the minor axis would produce a lower temperature rise distribution (i.e., lower applied energy density) among a larger number of sensors, than scanning along the minor axis, which will produce a higher temperature rise distribution among a smaller number of sensors, all other things being equal.

The use of multiple sensors 720, however, would require a substantial increase in the number of interconnecting wires in the cable coupling the applicator 600 and the power generator unit providing power to the applicator 600. The cost and complexity of this arrangement is further increased by the need for terminating circuits, one for each sensor 720 in the generator unit, to prevent any stray pickup of high voltage from the power conductors in the cable.

In one embodiment, the standoff 700 and/or the applicator 600 includes sensor data sampling, A/D conversion and serialization circuitry for the sensors 720 to solve the above-described problem. In this way, only one wire is required in the cable connecting the power generator unit to the applicator 600 for any number of sensors 720 included in standoff 700.

Figure 12:
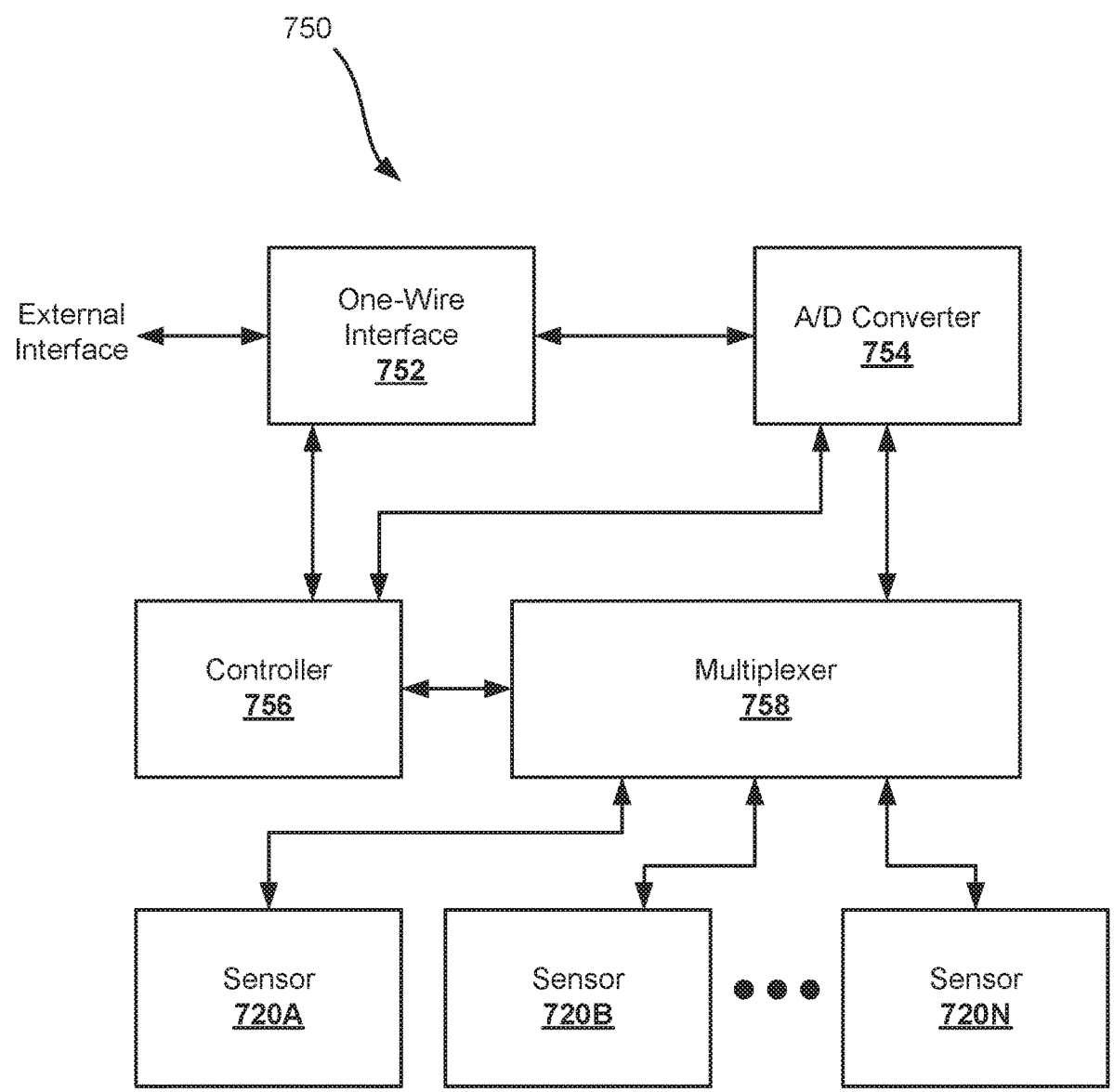
FIG. 12 is a block diagram of circuitry for the skin status monitoring apparatus of FIG. 8A in accordance with an embodiment of the present disclosure.

For example, referring to FIG. 12, circuit 750 is shown in accordance with the present disclosure. It is to be appreciated that some or all of the components of circuit 750 may be disposed in standoff 700, applicator 600, or a combination of the both devices 600 and 700. Circuit 750 includes a one-wire interface 752, an analog-to-digital (A/D) converter 754, a controller or processor 756, a multiplexer 758, and one or more sensors 720. Controller 756 is coupled to each of one-wire interface 752, A/D converter 754, and multiplexer 758. A/D converter 754 is also coupled to one-wire interface 752 and multiplexer 758. Multiplexer 758 is also coupled to each of sensors 720 and A/D converter 754. Circuit 750 is coupled to an external interface (e.g., an electrosurgical generator, such as, ESU 12) via one-wire interface 752.

In use, the output from each sensor 720 is sampled, either sequentially or in some other predetermined arrangement, by multiplexer 758. The output of multiplexer 758 from a given selected sensor 720 is then digitized by A/D converter 754 and then sent to one-wire interface 752, which is configured to serialize the digitized sensor data received. Controller 756 is configured to control each of the components of circuit 750 based on instructions stored in controller 756 or a memory coupled to controller 756. Since the digitized data associated with the measurements of sensors 720 is serialized by one-wire interface 752, only a single additional conductor coupled to the one-wire interface 752 is required in the cable coupling the applicator 600 to the generator unit (e.g., ESU 12) and only a single terminating circuit is required in the generator unit. If circuitry 750 is contained in the standoff device 700, communications and circuitry power may be established through a pair of electrical contacts between the standoff 700 and the applicator 600. For example, in one embodiment, the electrical contacts may be disposed or integrated with receiving portion 702 of standoff 700 and configured to mate with corresponding contacts on distal portion 602 of applicator 600. Applicator 600 is then configured to provide power to standoff 700 and receive communications from standoff 700 (e.g., sensor data) via the electrical contacts included in applicator 600 and standoff 700. Alternatively, the standoff circuits 700 may be coupled to a separate power source (e.g., batteries) and communicate directly to the generator unit through a RF or optical wireless means.

It is to be appreciated that the sensor data sampled from sensors 720 may be provided to a controller or processor of applicator 600 and/or a controller or processor of the generator unit coupled to applicator 600. As described above, the measurements from the sensor data may be used by a controller of applicator 600 and/or the generator unit to determine the applied energy density of a plasma beam 502 at a point of application 504 on the tissue surface 506 of a patient. Based on the determined applied energy density, the controller of the applicator 600 and/or the generator unit may adjust the power level of the plasma beam 502 (i.e., by adjusting the power applied to electrode 608) to maintain a predetermined applied energy density.

As described above, temperature measurements obtained from sensors 720 of the temperature on tissue surface 506 at the point of application 504 may be used by a controller of applicator 600 and/or a generator unit coupled to applicator 600 to determine applied energy density to the target tissue of a patient in real-time. The temperature measurements obtained from sensors 720 may also be used by a controller to determine the shape of the beam print 503 (e.g., an ellipse, in some embodiments) by the electrode 608 of applicator 600, the direction of movement of tip 604 of applicator 600 relative to a tissue surface 506, and the speed of movement of tip 604 of applicator 600 relative to a tissue surface 506. The determined temperature on tissue surface 506 at the point of application 504 may be used in conjunction with other known properties of plasma beam 502 (e.g., applied power level, gas flow rate, fixed distance between distal tip 604 and tissue surface 506, etc.) and the target tissue to maintain the applied energy density to the target tissue within a beneficial range to produce the desired physiological effect. There are a number of physical relationships that may be used to take the temperature data and ultimately compute a proper power setting for the applicator 600 to maintain the desired physiological effect within the beneficial range. However, this computation-intensive approach would require considerable CPU speed, particularly since a real-time response is essential. A preferred approach is to store various temperature data/power setting relationships in a lookup table (e.g., in a memory of applicator 600 or ESU 12), enabling fast real-time response. The contents of this lookup table can be pre-determined off line by a computation intensive approach, by experimental data, or some combination thereof.

For example, if it is determined by the controller that the current applied energy density has fallen below the beneficial range or predetermined value or threshold, the controller is configured to transmit a signal to the generator unit to increase the applied power to the plasma beam 502 until the applied energy density is increased to be within the beneficial range. Alternatively, if it is determined by the controller that the current applied energy density has exceeded the beneficial range, the controller is configured to transmit a signal to the generator unit to decrease the applied power to the plasma beam 502 until the applied energy density is decreased to be within the beneficial range. In this way the controller is configured to continuously determine the applied energy density in real-time, and increase or decrease the applied energy density (by instructing the generator unit to increase or decrease the applied power level of plasma beam 502) as needed based on the determined applied energy density to maintain the applied energy density within the beneficial range. It is to be appreciated that the beneficial range may vary for different procedures and target tissues. The beneficial range for a given procedure and target tissue may be predetermined and stored in a memory of either applicator 600 and/or the generator unit.

A different approach can be used to monitor the effects of energy deposition on a target tissue site with a cold plasma jet applicator 600 by measuring the change in tissue impedance through the conductive nature of the cold plasma beam 502 itself. This requires measurement of the plasma beam voltage and current. Ideally, these measurements could be conveniently made in the generator unit 12. However, variable losses in the cable wires 30 and 32, depending on the position and location of the cable in the surrounding environment, may require the plasma beam voltage and current measurements to be made directly in the applicator 600.

Figure 13A:
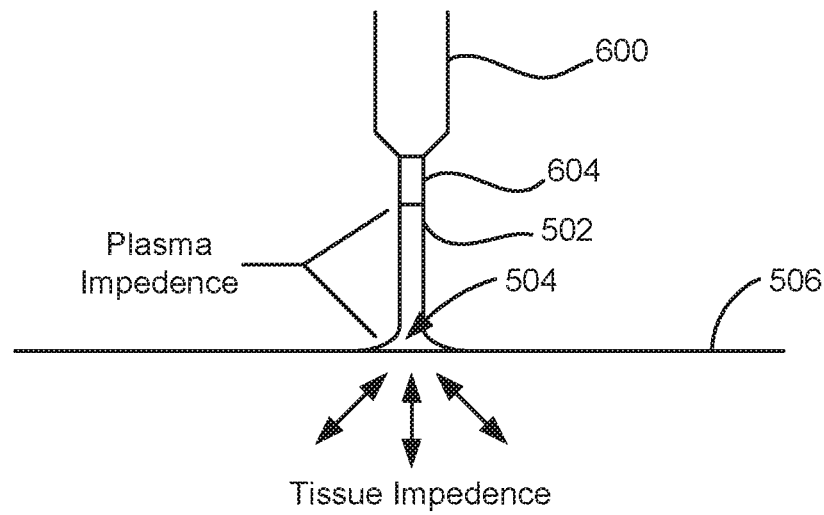
FIG. 13A is illustrates the plasma impedance of a cold plasma beam generated by an electrosurgical apparatus and the tissue impedance of a target tissue site in accordance with an embodiment of the present disclosure.
Figure 13B:
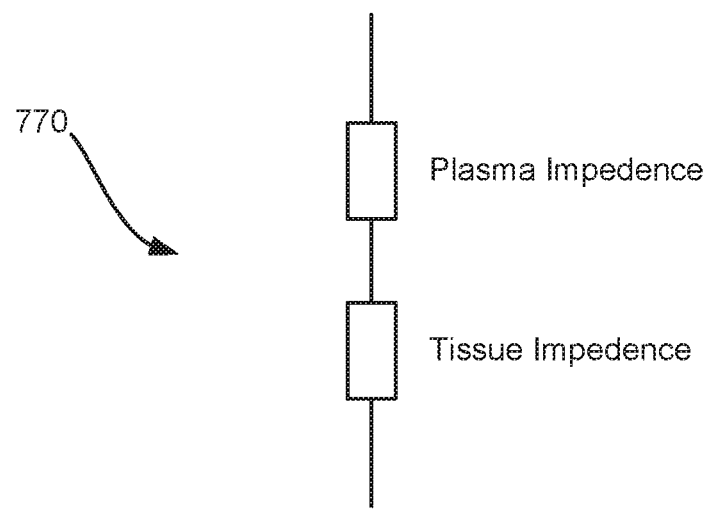
FIG. 13B is an equivalent circuit of the plasma impedance and tissue impedance shown in FIG. 13A in accordance with an embodiment of the present disclosure.

This principle is illustrated in FIGS. 13A and 13B, where FIG. 13A shows how the total impedance, measured at the applicator tip 604, is the sum of the cold plasma beam impedance and the tissue impedance, and FIG. 13B is the equivalent circuit 770. It is to be appreciated that, in one embodiment, the beam impedance is measured or sensed at the applicator tip 604 by one or more sensors (e.g., voltage and/or current sensors) disposed in the applicator tip 604. In another embodiment, the beam impedance is measured or sensed by sensors in the electrosurgical generator (e.g., ESU 12) coupled to applicator 600 by sampling the current and voltage outputted by the electrosurgical generator to the applicator 600. In either case, a potential problem with this approach is that the cold plasma beam impedance is very sensitive to the distance between the applicator tip 604 and the surface 506 of the target tissue site. As this distance is reduced, the plasma impedance decreases. However, by using the fixed distance standoff device 700 of the present disclosure, the distance between the applicator 600 and the tissue also remains fixed and is thus known. For a given set of conditions of applied power level, carrier gas flow rate, and distance between the distal tip 604 of applicator 600 and tissue surface 506, the known plasma impedance can be subtracted (e.g., by a controller/processor of applicator 600 or ESU 12) from the total impedance (sum of plasma and tissue impedance) measured from the applicator tip 604 or ESU 12 to calculate the tissue impedance.

Figure 14:
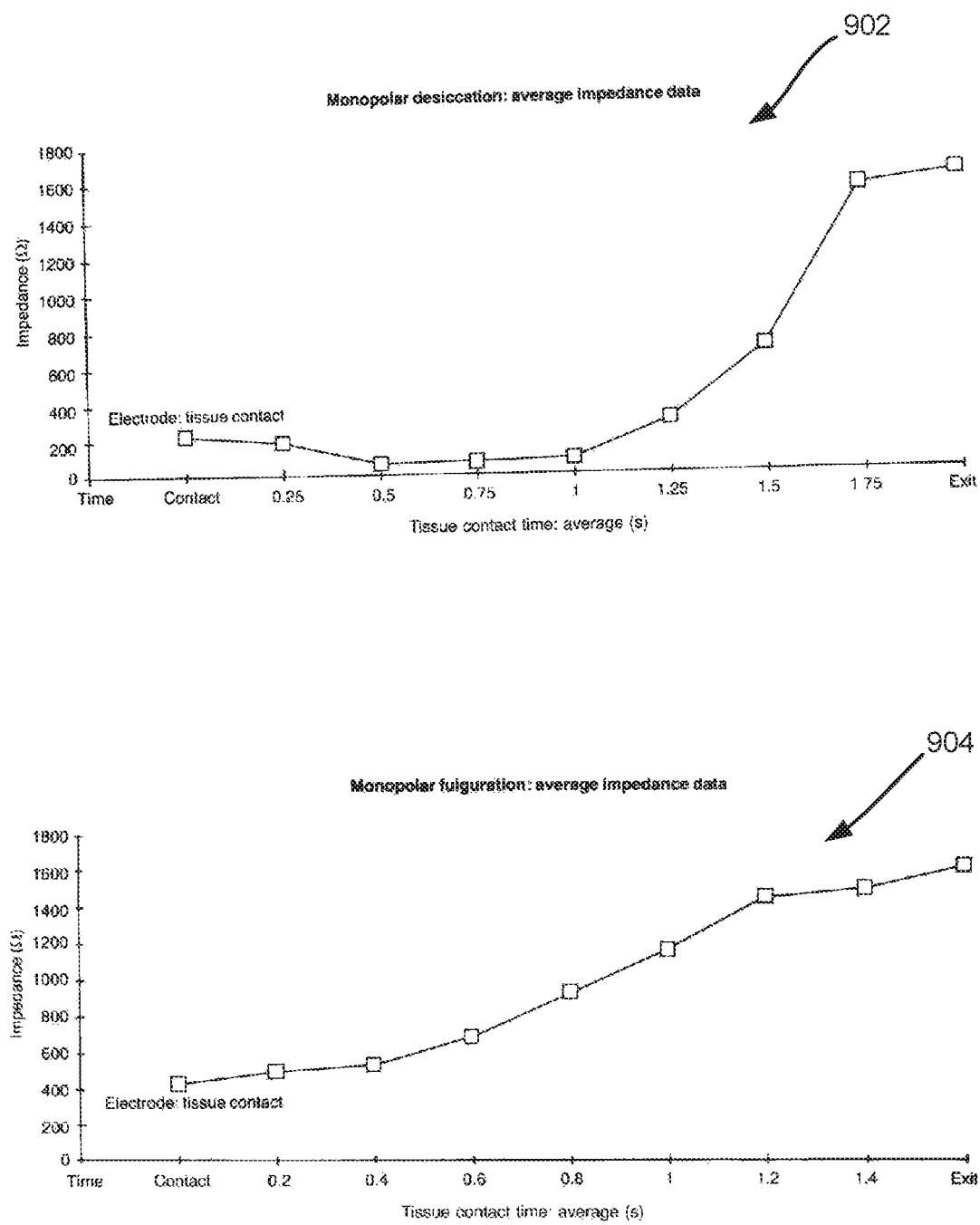
FIG. 14 includes graphs showing changes in tissue impedance under various electrosurgical conditions in accordance with an embodiment of the present disclosure.

Referring to FIG. 14, graphs 902 and 904 are shown in accordance with the present disclosure. Graphs 902 and 904 show typical changes in tissue impedance under electrosurgical conditions using 80 Watts (graph 902) and 40 Watts (graph 904). As energy is applied to the target tissue site 506, the tissue gradually desiccates and its impedance increases. This impedance change can be used by a controller of applicator 600 and/or the generator unit to modify the applied power level of beam 502 to maintain a constant physiological effect, particularly while the applicator 600 is being scanned, or to stop further application of energy when a desired physiological endpoint is reached in a stationary applicator mode. For example, as the total calculated impedance increases, the applied power is decreased.

In another embodiment of the present disclosure, another method to measure subtle tissue changes under applied energy using a cold plasma beam is to monitor the changes in phase shift between voltage and current of the plasma beam 502. It is to be appreciated that, in one embodiment, voltage and current of the plasma beam 502 are measured or sensed at the applicator tip 604 by one or more sensors (e.g., voltage and/or current sensors) disposed in the applicator tip 604. In another embodiment, voltage and current of the plasma beam 502 are measured or sensed by sensors in the electrosurgical generator (e.g., ESU 12) coupled to applicator 600 by sampling the current and voltage outputted by the electrosurgical generator to the applicator 600. In either case, the phase shift between the voltage and current of the plasma beam 502 is calculated by a controller of applicator 600 or the electrosurgical generator based on the voltage and current measurements acquired.

The voltage and current phase relationship of the plasma beam 502 depends on the equivalent dielectric constant of the target tissue site. The equivalent dielectric constant will change both with the level of desiccation and bulk tissue temperature at the application site. Using a comparison to a predetermined expected phase relationship for a desired physiological effect, the applied power can be adjusted (e.g., by a controller of applicator 600 and/or the generator unit) using the measured phase shift as a feedback signal. Untreated tissue will have a combination of resistive and capacitive components producing a fixed phase shift, whose actual value will depend on the frequency of the plasma beam. A lower frequency plasma beam will have the capacitive component dominate, while a higher frequency one will have the resistive component dominate. This is due to the capacitive reactance varying inversely with frequency. At higher frequencies, the capacitive reactance becomes smaller. However, as the tissue desiccates, it becomes increasingly capacitive. So, for a given plasma beam frequency, as the tissue desiccates, the phase shift will increase.

Figure 15:
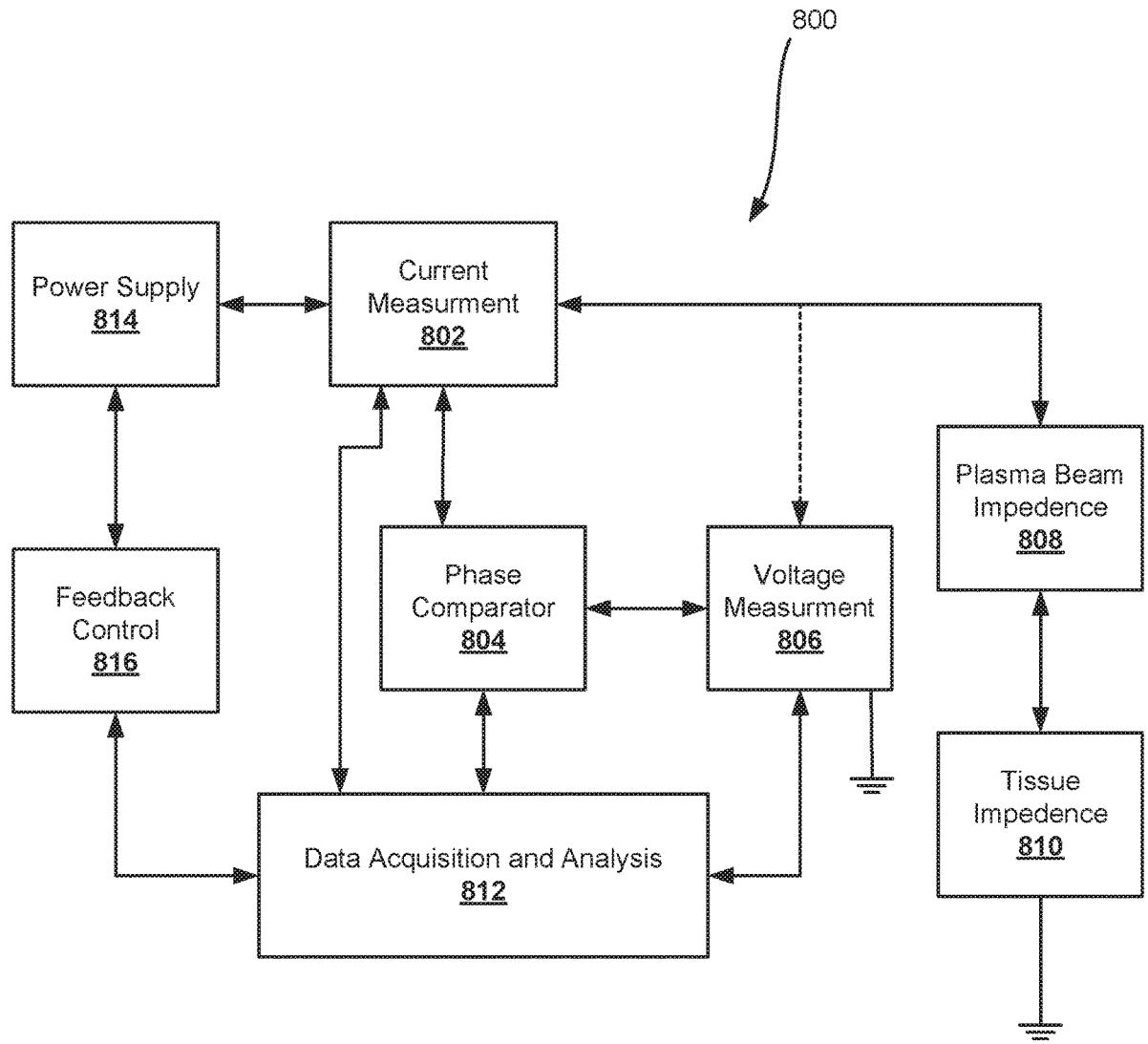
FIG. 15 is a block diagram of a circuit in accordance with an embodiment of the present disclosure.

For example, referring to FIG. 15, a block diagram of a circuit 800 is shown in accordance with the present disclosure. Circuit 800 includes a current measurement module 802, a phase comparator 804, a voltage measurement module 806, a plasma beam impedance module 808, a tissue impedance module 810, a data acquisition and analysis module or processor 812, a feedback control module 816, and a cold plasma power supply 814. It is to be appreciated that some or all of the components of circuit 800 may be disposed in applicator 600, device 700, and/or a generator unit (e.g., ESU 12) coupled to applicator 600.

Power is provided via a cold plasma power supply 814 (e.g., an electrosurgical generator) to applicator 600 to generate a plasma beam 502. Current measurement module 802 (e.g., a current sensor) and voltage measurement module (e.g., a voltage sensor) 806 are configured to measure the current and voltage, respectively, of a plasma beam 502 being applied to a tissue site 506 based on the power provided by cold plasma power supply 814 to applicator 600. The voltage and current measurements of modules 806, 802 are then provided to phase comparator 804. Phase comparator 804 is configured to determine the phase shift between voltage and current of the plasma beam 502 and provide the determined phase shift to data acquisition and analysis module 812. Based on the phase shift data received from phase comparator 804, module 812 is configured to determine if a predetermined change in phase shift has occurred between the voltage and current of plasma beam 502 indicating a change in applied energy density of the plasma beam 502. If a predetermined change in phase shift is determined to have occurred by module 812, a signal indicative of the change in phase shift is provided by module 812 to feedback control 816. It is to be appreciated that the module 812 may determine an amount the power level of the plasma beam 502 needs to be altered, i.e., an amount the power level needs to be increased or decreased by to maintain a desired level of applied energy density. The signal provided to feedback control 816 may include this determination by module 812. Based on the signal provided to feedback control 816, the power provided by cold plasma power supply 814 to applicator 600 may be adjusted to increase or decrease the applied energy density as desired to maintain a desired physiological effect on a target tissue site. Feedback control module 816 may contain a look up table that converts a specific phase shift value to an alteration in applied power level, given a specific baseline power setting and gas flow rate. For example, a small phase shift at a low power setting may only require a small adjustment in applied power, while the same phase shift at a high applied power setting may require a much larger adjustment to maintain the desired physiological effect.

Modules 808 and 810 represent the actual electrical impedance characteristics of the plasma beam and tissue respectively and are equivalent to FIG. 13B. Since the phase shift of tissue impedance 810 is measured through the plasma beam impedance 808, the total phase shift measured by the phase comparator 804 will be the sum of phase shifts introduced by the plasma beam impedance 808 and the tissue impedance 810. However, the plasma beam 502 is generally operated in a direct discharge, attached beam mode where a continuous conductive plasma channel exists between the applicator 600 and the target tissue site 504. Under this condition, the plasma beam impedance 808 is essentially resistive and introduces little or no additional phase shift itself. As such, the phase shift measured by the phase comparator 804 will primarily be that of the tissue impedance 810. On the other hand, there may be circumstances where plasma beam 502 is not operated in the direct contact mode and will exhibit both resistive and capacitive components. This will introduce a phase shift from the plasma beam impedance 808 in addition to the tissue impedance 810 phase shift. The phase shift introduced by the plasma beam impedance 808 in the non-contact mode can be determined experimentally, then stored and subtracted by data acquisition and analysis module 812 from the measured value provided by phase comparator 804. The additional phase shift introduced by a non-contact plasma beam remains fixed for a given set of operating conditions, such as power level, gas flow rate, and distance from the applicator to the tissue surface. If these conditions remain fixed, the additional phase shift of the plasma beam can be considered as a fixed offset to the variable phase shift of the desiccating tissue.

Figure 16:
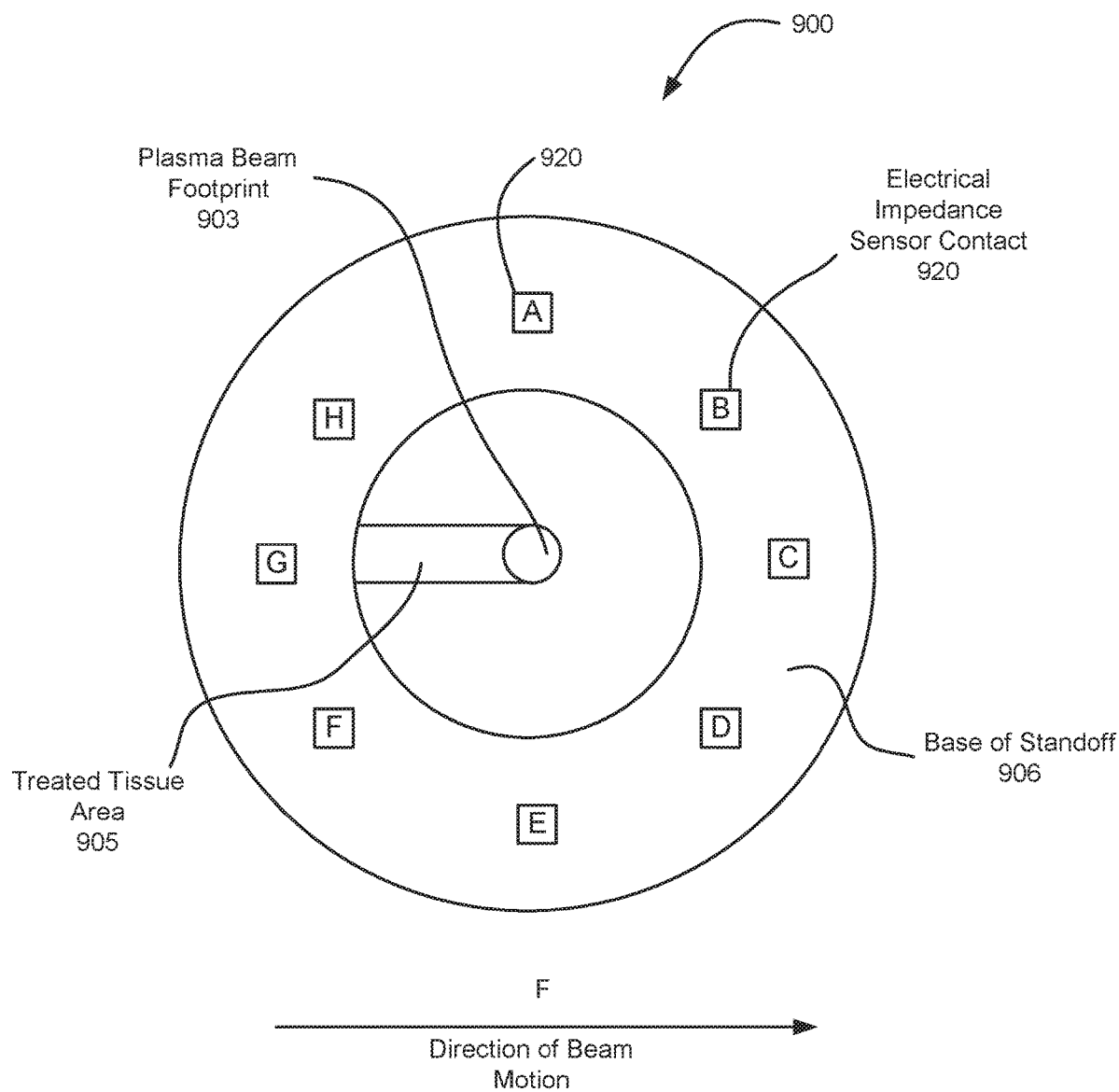
FIG. 16 illustrates an array of electrodes disposed on a base of a standoff in accordance with an embodiment of the present disclosure.

In another embodiment, the electrical tissue impedance can be measured by direct contact electrodes or impedance sensors. FIG. 16 illustrates an array of electrodes 920 (e.g., electrodes A, B, C, D, E, F, G, H) that may be placed or disposed on base 906 of standoff 900 and would be in direct contact with the skin. It is to be appreciated that standoff 900 is configured in the same manner (e.g., including a receiving portion, posts, and a base) as standoff 700. In addition, FIG. 16 includes a typical plasma beam footprint 903 and associated track of treated tissue 905 as the device is scanned to the right, as indicated by arrow F. The electrical tissue impedance is determined by selecting a particular pair of electrodes 920. By selecting, for example, electrodes A and E in FIG. 16, the electrical impedance directly under the beam footprint 903, in addition to other tissue along this path, can be probed. Selecting electrodes C and G will probe both the tissue under the beam footprint 903 plus the treated tissue track 905. The electrode combinations B and C, C and D, or B and D can probe untreated tissue ahead of the beam's path. Electrodes H and F can probe only treated tissue after the beam has passed over it. In this way, the direction and orientation of the applicator can be determined by a controller in the applicator or electrosurgical generator in communication with electrodes 920. The speed of the applicator may also be derived by the controller using a previously determined relationship (e.g., experimentally, computationally, or both) between the change in tissue electrical impedance and the applied energy density. Since the applied energy density depends on the applied power level and the dwell time, and therefore applicator speed, knowing the change in electrical impedance and the applied power level, the applicator speed may be determined, e.g., by the controller or a measurement system 950 (shown in FIG. 17) as will be described below. The change in electrical impedance, between treated and untreated tissue, is used by a controller in applicator 600 or ESU 12 to relate to a physiologically beneficial, insufficient, or damaging effect and provide a feedback signal to correct the applied power level to remain within a beneficial effect.

Figure 17:
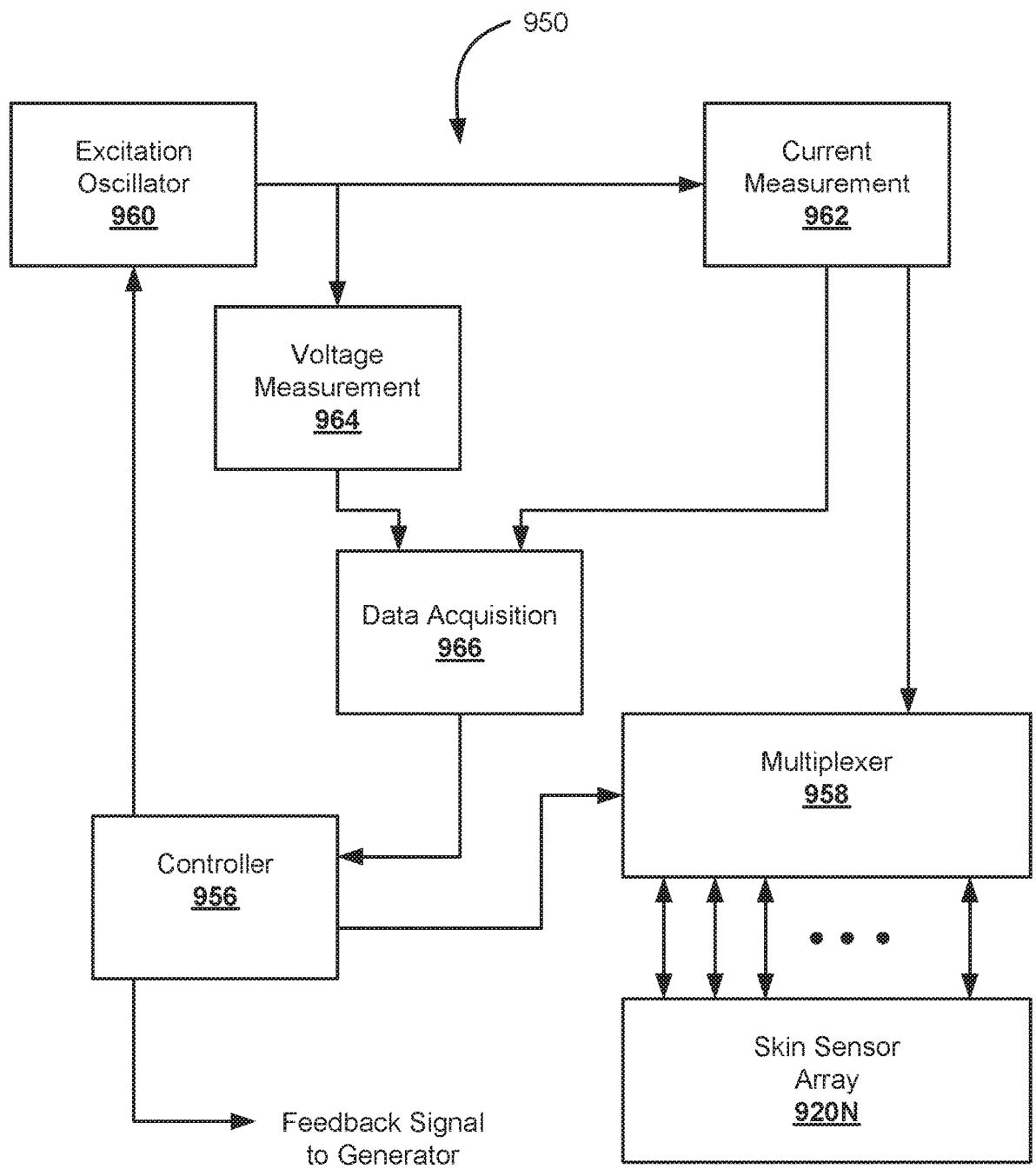
FIG. 17 is a block diagram of a tissue electrical impedance measurement system in accordance with an embodiment of the present disclosure.

A block diagram of the tissue electrical impedance measurement system 950 is shown in FIG. 17. A pair of electrodes, e.g., from electrode array 920, in the skin sensor array is selected by the multiplexer 958. A probe signal from the excitation oscillator 960 is applied to the selected pair of electrodes through the multiplexer 958 while taking both current measurements and voltage measurements of the selected pair of electrodes via current measurement module 962 and voltage measurement module 964, respectively. The probe signal is typically on the order of a few hundred millivolts and may range in frequency from a few kHz to a few MHz. The specific excitation voltage amplitude and frequency is selected by the controller 956 and may be adjusted to optimize the probe signal under varying conditions. For example, dry skin would require a higher amplitude, higher frequency probe signal, as would highly desiccated tissue. If a saline solution is applied to the skin, a lower amplitude, lower frequency would be preferred.

The voltage and current measurements are digitized by the data acquisition module 966 and fed to the controller 956. The controller 956 computes the tissue impedance as the ratio of voltage to current. By noting the relative timing of the peak voltage and/or zero crossing of the voltage and current measurements, the phase shift between the two measurements can be determined by controller 956. Using a previously determined relationship between impedance change and/or phase shift with physiological effect, a feedback signal is developed by the controller 956, which is used to adjust the applied power level produced by the generator and applied to the electrode of the applicator. For example, if the impedance change is too small as determined by controller 956, indicating a physiologically insufficient effect, controller 956 sends a feedback signal to the generator to increase the applied power level to the applicator 600. If the impedance change is too large as determined by controller 956, indicating a physiologically damaging effect, controller 956 sends a feedback signal to the generator to decrease the applied power level to the applicator 600. It is to be appreciated that some or all of the components of circuit 950 may be disposed in applicator 600, device 700, and/or a generator unit (e.g., ESU 12) coupled to applicator 600.

Acoustic impedance is another form of measurement that can be used to assess the degree of physiological effect of plasma energy applied to tissue. It may result in tissue shrinkage which produces an increase in tissue density, acoustic impedance, and speed of sound propagation. It is this last parameter, i.e., speed of sound propagation in tissue, that is most easily measured and used as a proxy for the degree of physiological effect.

Figure 18:
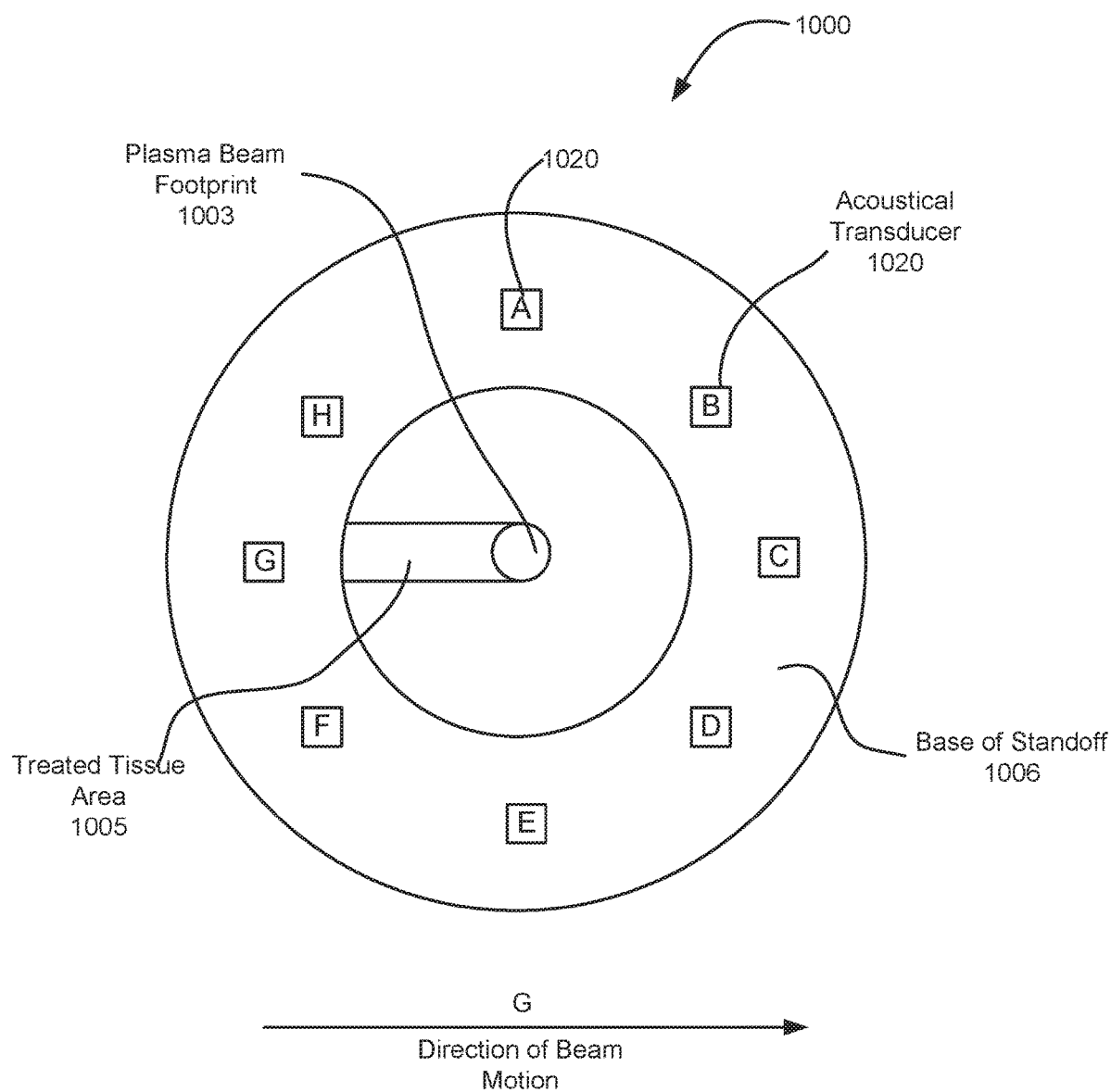
FIG. 18 illustrates an array of acoustical transducers disposed on a base of a standoff in accordance with an embodiment of the present disclosure.

FIG. 18 illustrates a standoff device 1000 including an arrangement of acoustic transducers 1020 disposed around the base 1006 of standoff 1000, where the acoustic transducers 1020 are in direct contact with the tissue surface when the base 1006 of standoff 1000 is in contact with the tissue surface. It is to be appreciated that standoff 1000 is configured in a similar manner as standoff 700 (e.g., including a receiving portion, posts, and a base) described above. Also shown in FIG. 18 are a representative plasma beam footprint 1003 and associated track of treated tissue 1005 as the applicator is scanned across the tissue surface, e.g., in a direction of beam motion as indicated by arrow G. An electrical impulse or oscillation is applied to a given transducer 1020, causing it to emit an acoustical emission. A second selected transducer 1020 then receives this acoustical emission, which converts it back into an electrical signal and is then amplified. Knowing the distance between these transducers and the time-of-flight for the acoustical emission between them, the acoustical velocity along that path can be calculated by a controller in applicator 600 or ESU 12. By selecting various emitter and receiver transducer combinations, different paths through the tissue between them can be acoustically characterized. By selecting, for example, transducers A and E in FIG. 18, the acoustical impedance directly under the beam footprint 1003, in addition to other tissue along this path, can be characterized. Selecting transducers C and G will characterize both the tissue under the beam footprint 1003 plus the treated tissue track 1005. The transducer combinations B and C, C and D, or B and D can characterize untreated tissue ahead of the beam's path. Transducers H and F can probe only treated tissue after the beam has passed over it. Similar to the electrical impedance approach described above, in the current acoustical transducer approach the direction and orientation of the applicator can be determined by the controller using acoustical impedance data acquired via acoustical transducers 1020. The speed of the applicator can also be derived by the controller using a previously determined relationship (e.g., experimentally, computationally, or both) between the change in tissue acoustical impedance and the applied energy density. Since the applied energy density depends on the applied power level and the dwell time, and therefore applicator speed, knowing the change in acoustical impedance and the applied power level, the applicator speed may be determined. The change in acoustical impedance, between treated and untreated tissue, is used by the controller to relate to a physiologically beneficial, insufficient, or damaging effect and provide a feedback signal to generator or ESU 12 to correct the applied power level to remain within a beneficial effect.

In addition to time-of-flight acoustical characterization, differential acoustical absorption along various acoustical transducer pairs can be used by the controller to assess the physiological state of the tissue along that path. Treated tissue may have different acoustical absorption characteristics than untreated tissue, depending on the degree of treatment. An acoustical signal sent along a path with higher acoustical absorption will appear weaker at the receiving transducer than a signal sent along a path with less absorption. This differential degree of acoustical signal weakening can then be used by the controller to determine the physiological state of treated versus untreated tissue and produce a feedback signal provided to ESU 12 to adjust the generator applied power level to applicator 600.

Figure 19:
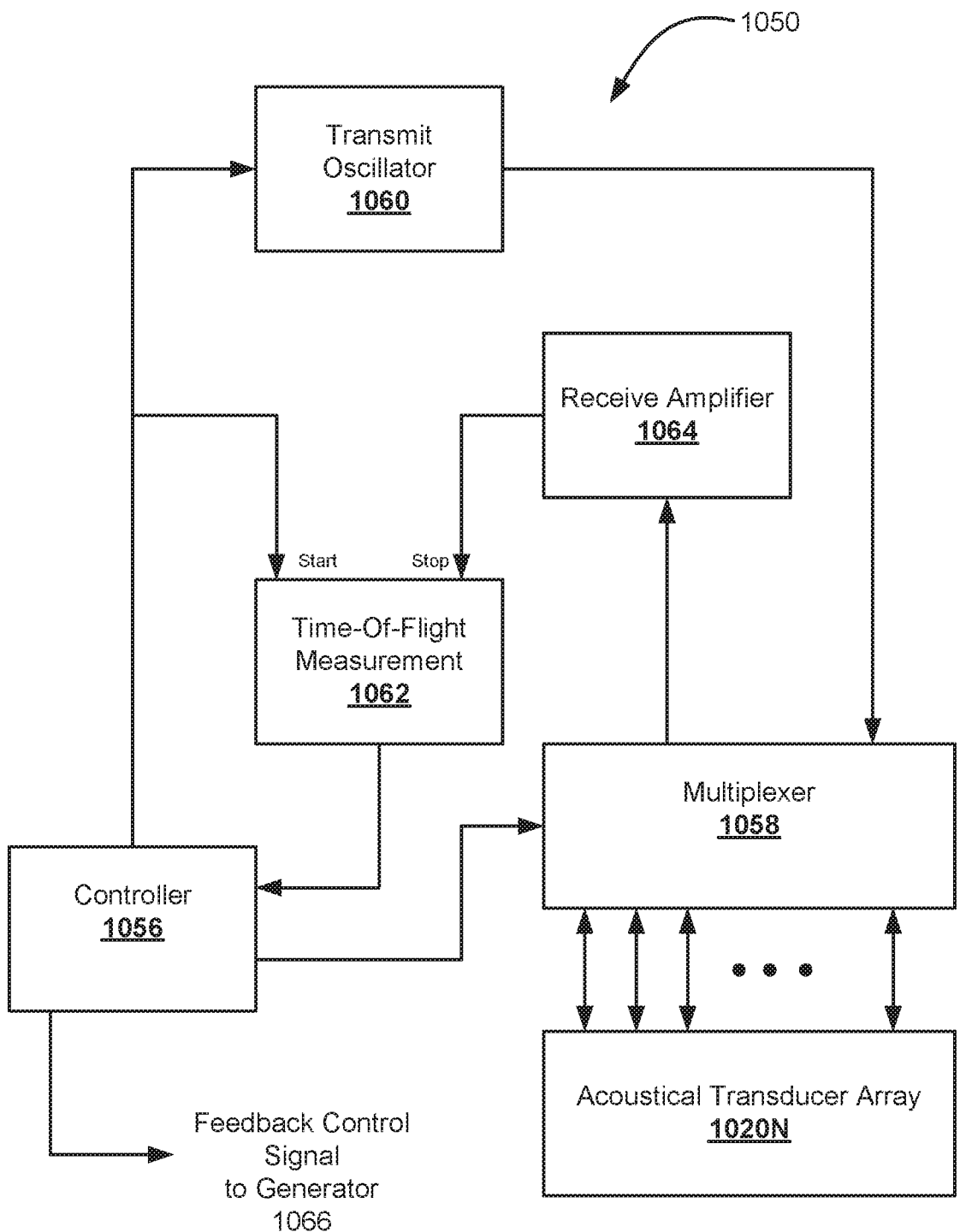
FIG. 19 is a block diagram of an acoustical impedance measuring system in accordance with an embodiment of the present disclosure.

A block diagram of an acoustical impedance measuring system 1050 for use with standoff 1000 is shown in FIG. 19 in accordance with the present disclosure. A multiplexer 1058, under direction of a controller 1056, selects a given emitter and receiver transducer pair from the transducer array 1020, e.g., transduces A-H (shown in FIG. 18). The controller 1056 then initiates a transmit oscillator 1060 to send a signal to the selected emitter transducer in the pair, while also initiating a time-of-flight measurement module 1062, essentially starting a timer. When the selected receiver transducer of the pair picks up the acoustical emission, this signal is amplified by the receiver amplifier 1064 and then used to stop the time-of-flight timer. The time-of-flight value is then sent for time-of-flight measurement module 1062 to the controller 1056, which then uses a previously determined relationship (e.g., stored in a lookup table) to produce a feedback signal 1066 that is provided to the generator or ESU 12 for the generator to adjust the applied power level, if necessary. It is to be appreciated that some or all of the components of circuit 1050 may be disposed in applicator 600, device 700, and/or a generator unit (e.g., ESU 12) coupled to applicator 600.

Figure 20:
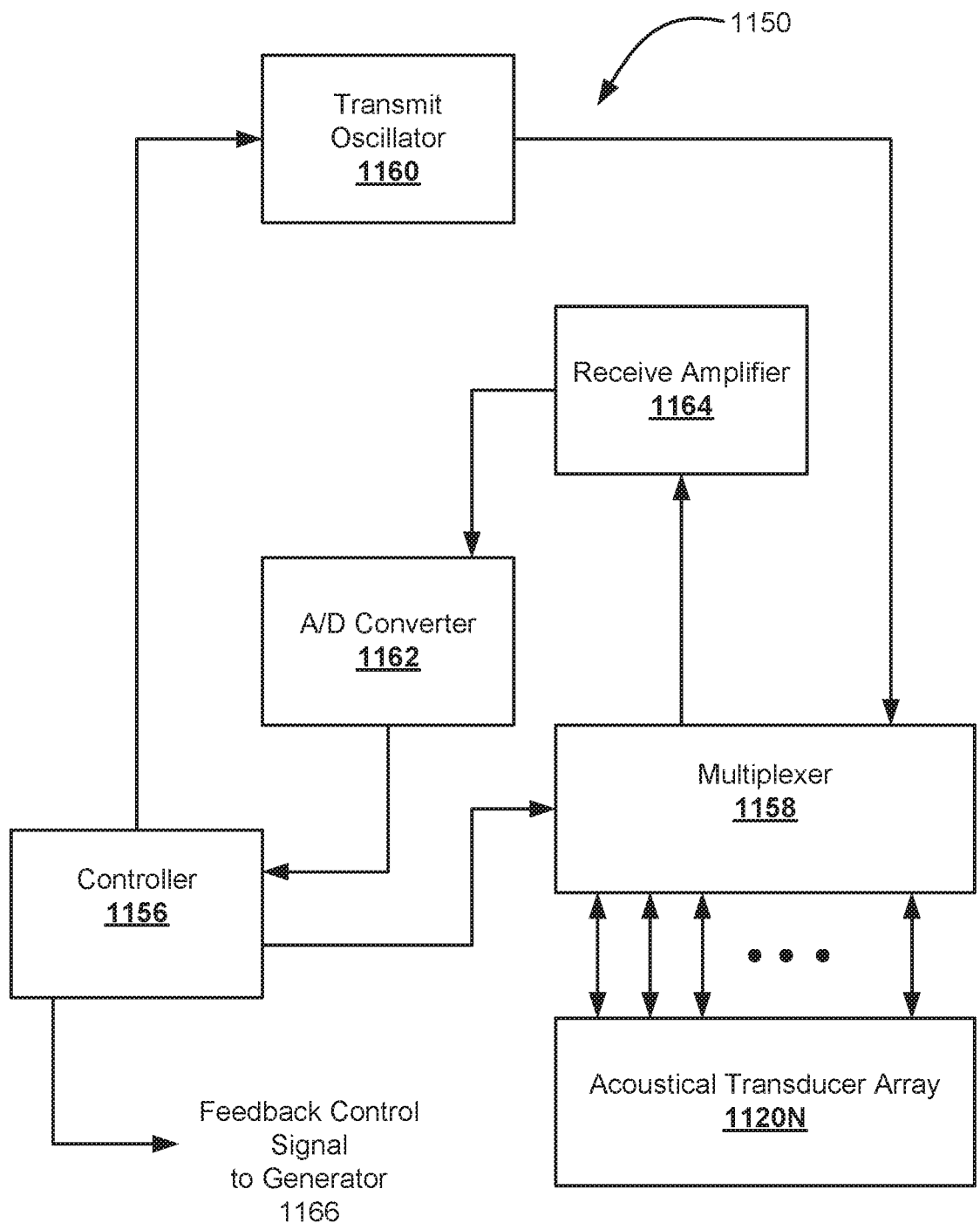
FIG. 20 is a block diagram of a differential acoustical absorption measuring system in accordance with an embodiment of the present disclosure.

A block diagram of a system 1150 for use with standoff device 1000 to measure differential acoustical absorption is shown in FIG. 20 in accordance with the present disclosure. A multiplexer 1158, under direction of a controller 1156, selects a given emitter and receiver transducer pair from the transducer array 1120. The controller 1156 then initiates a transmit oscillator 1160 to send a signal to the selected emitter transducer of the pair. The selected receiver transducer of the pair has its output amplified by a receiver amplifier 1164, which is then digitized by an A/D converter 1162 and sent to the controller 1156. The controller 1156 selects various transducer pairs to characterize the acoustical absorption of the path between the selected transducer pair by comparing the amplitude (i.e., strength) of the received acoustical signal along that path. Based on the differential acoustical absorption along treated and untreated tissue pathways, a feedback signal 1166 is developed and provided to generator or ESU 12 by controller 1156 to adjust the applied power level produced by the generator. It is to be appreciated that some or all of the components of circuit 1150 may be disposed in applicator 600, device 700, and/or a generator unit (e.g., ESU 12) coupled to applicator 600.

As will be described in greater detail below, in other embodiments of the present disclosure, an applicator may be provided having an emission collector (e.g., a sound tube, optical fiber, etc.) configured to collect emissions (e.g., acoustical emission, optical spectra, etc.) associated with the plasma beam generated and/or tissue surface. The collected emissions are used by a controller or processor (e.g., disposed in the applicator or an electrosurgical unit coupled to the applicator) to output a feedback signal to the electrosurgical generator to adjust the applied power level of the plasma beam based on the collected emissions.

For example in a somewhat different approach, the acoustical emissions of the plasma beam itself can be used to assess the physiological state of the tissue under the plasma beam, and the frequency of these acoustic emissions may be used to develop a feedback signal to adjust the applied power level of the generator and thus of the plasma beam.

It has been observed that under various conditions of plasma beam power setting, gas flow rate, and distance of the applicator tip from the applied surface, an acoustic emission is produced by the plasma beam. Under certain conditions, this acoustic emission is audible. Furthermore, as the distance from the applicator tip to the applied surface is decreased, the acoustic emission frequency increases. If the applicator distance, power setting and gas flow rate are held constant, the addition of vaporized water and other vaporized tissue components from tissue being treated can alter the frequency of this plasma acoustic emission. This change in frequency may be used to monitor the physiological state of the tissue being treated and also be used to develop a feedback signal generated by a controller to adjust the power setting of the generator to maintain a beneficial physiological effect.

Plasma beam acoustic emissions can arise from a flow resistance effect produced by a plasma discharge. It is observed that the back-pressure of a plasma applicator is lower when only gas is flowing and no plasma is present. When the plasma beam is activated, the back-pressure can increase by several percent, depending on the power setting. The higher the plasma power setting, the greater the back-pressure. Parcels of gas flowing from the applicator nozzle can become trapped in the center of the plasma beam by this back-pressure effect, especially near the target application surface. Normally, gas flowing from the applicator nozzle interacts with the plasma beam only briefly before flowing away from the application site. This gas flowing in the plasma beam experiences plasma heating only briefly during that transit time between the nozzle and target surface. However, if some of the gas becomes trapped by plasma confinement, it will continue to heat and expand until this gas expansion pressure equals or exceeds the plasma confinement back-pressure. At this point, the trapped parcel of gas vents through the plasma confinement walls and produces an acoustical emission in the process. After this back-pressure is relieved, the process can start over again with a new parcel of gas, going through the same cycle of confinement, pressure buildup and venting. This process is referred to as a relaxation oscillator. The periodicity of this recurring cycle gives rise to a plasma acoustical emission frequency which is dependent on the strength of the plasma confinement (i.e., applied power setting) and the gas flow rate (i.e., trapped gas parcel expansion rate). Decreasing the distance of the applicator nozzle to the target surface also reduces the plasma beam impedance, heating the trapped gas faster and thereby also increases the plasma acoustical emission frequency. However, if the applicator distance, applied power setting, and gas flow rate are kept constant, the plasma acoustical emission frequency is constant due to a fixed period relaxation oscillation process.

If an additional gas source is added to the trapped gas parcel, the rate of expansion increases (i.e., more gas to expand), the relaxation period decreases, so the plasma acoustical emission frequency increases. As the plasma beam interacts with a tissue surface, volatile components of the tissue are released, including water vapor, vaporized tissue components, and so on. These volatized components act as an additional gas source to the trapped gas parcel and cause the plasma acoustical emission frequency to increase. The degree of frequency increase is proportional to the rate of the introduction of volatilized components. In this way, the change in the plasma acoustical emission frequency may be used by a controller as an indicator of physiological effect and used by the controller to derive a feedback signal to adjust the applied power setting of the generator to maintain a beneficial effect.

Figure 21:
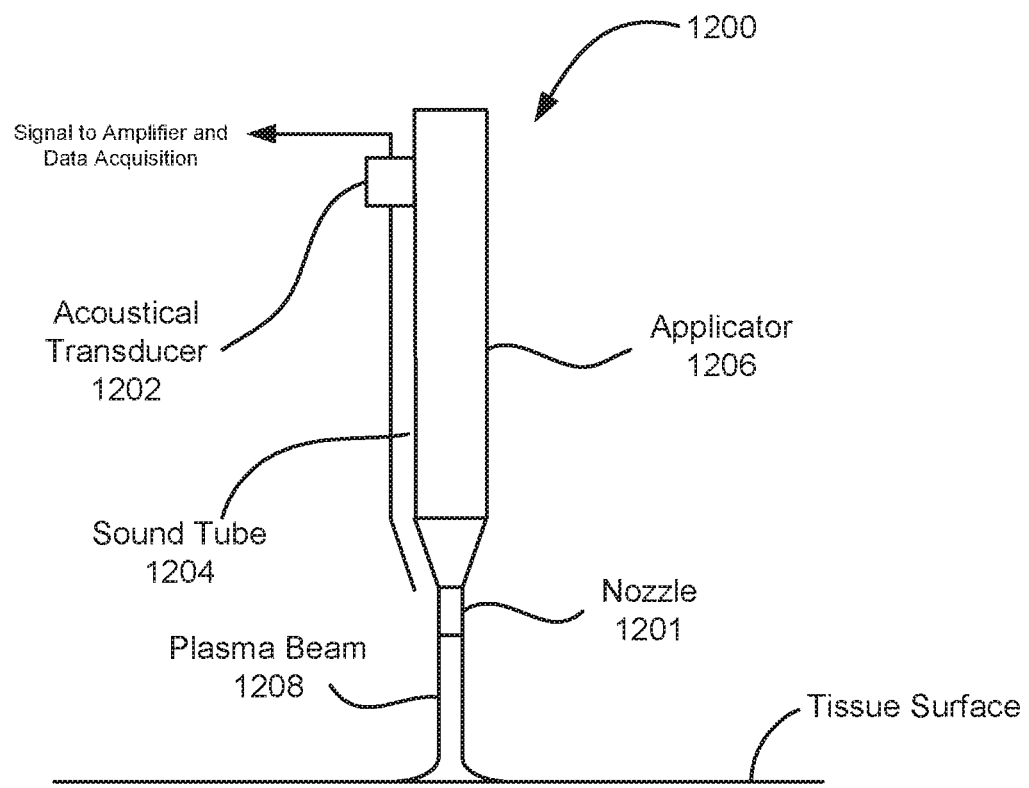
FIG. 21 illustrates an apparatus for measuring plasma acoustical emissions in accordance with an embodiment of the present disclosure.

FIG. 21 shows a setup 1200, where the plasma acoustical emissions can be monitored and used to derive a feedback control signal in accordance with the present disclosure. In the setup of FIG. 21, an applicator 1206 is provided including a nozzle or distal tip 1201, an acoustical transducer 1202, and a sound tube 1204. The acoustical transducer 1202 is configured to convert the plasma acoustical emission frequency of acoustical emissions received via sound tube 1204 into an electrical signal and produces a relatively low level electrical output, typically on the order of millivolts. To minimize interference of radiated emissions from the plasma beam, which typically operates at several hundreds to thousands of volts, a non-conductive sound tube 1204, coupled to applicator 1206, is used to convey the plasma acoustical emissions from to the plasma beam 1208 to a remotely located (i.e., away from the plasma beam 1208) acoustical transducer 1202. The sound tube 1204 and transducer 1202 may be disposed on and/or integrated with an exterior portion of the housing, with a proximal end of the tube 1204 having an open end for receiving acoustical emissions and the distal end of the tube coupled to the acoustical transducer 1002. Transducer 1202 may be powered by applicator 1206 or an independent power source (e.g., batteries, an external power supply, etc.) The output from the acoustical transducer 1202 is amplified (e.g., by an amplifier) and digitized (e.g., by an A/D converter) and then used by a controller to develop a feedback signal that is provided to the generator. The amplifier, A/D converter and controller may be co-located with the acoustical transducer 1202, minimizing the number of additional wires that need to be added to the cable connecting the applicator 1206 to the generator unit.

In another embodiment, optical emission spectra from a plasma beam can be used by a controller to develop a feedback signal that adjusts the applied power level of the generator and thus the applied power level of the plasma beam to maintain the physiological effect within the beneficial range. As the plasma beam interacts with the target tissue, and volatile tissue components are released, some of the volatile tissue components will interact with the plasma beam and become ionized. When electrons recombine with these ions, characteristic optical spectra are generated. In some cases, simply the presence of a given spectral component will be sufficient to act as a signal that the applied energy density is too high. In other cases, the strength of the volatile tissue component-derived emission spectra can be used to derive a feedback signal to control the generator's applied power level. For example, if these emission spectra are too weak, the applied power level would be increased, and vice versa.

It is important that selected emission spectral lines be chosen so they will not be confused with emission lines of the carrier gas, such as helium or argon, or with those produced by the plasma beam interaction with ambient air. These include oxygen species, nitrogen species, oxy-nitrogen species, hydroxyl radicals and so on.

Figure 22:
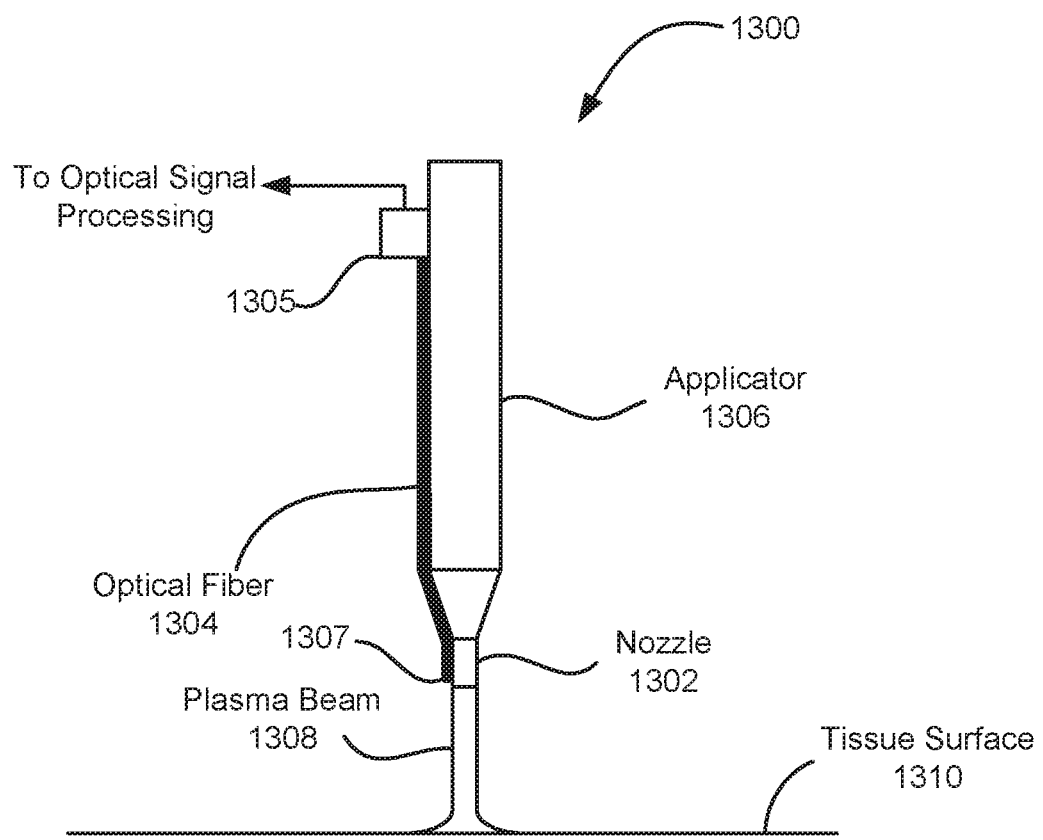
FIG. 22 illustrates an apparatus for measuring plasma emission spectra in accordance with an embodiment of the present disclosure.

FIG. 22 illustrates a setup 1300 including an applicator 1306 having, an applicator nozzle tip 1302 and an optical fiber 1304 in accordance with the present disclosure. The optical fiber 1304 includes a tip or end 1307 that is used to collect emission spectra from the proximity of the applicator nozzle tip 1302 and provide the emission spectra to an optical signal processor 1305 in applicator 1306 or a generator or ESU 12 coupled to applicator 1306. Due to turbulence effects of the gas flow around the plasma beam 1308, the specific location of the optical fiber tip 1307 of fiber 1304 around the periphery of the nozzle 1302 is not important as the tissue-derived optical emission spectra tend to be uniformly distributed in the plasma beam footprint. However, it is important to have the optical fiber tip 1307 of fiber 1304 close to the exit of applicator nozzle 1302 to maximize the light gathering ability of the tip 1307 of fiber 1304. The optical fiber 1304 in FIG. 22 is shown located externally to the applicator 1306 (e.g., outside of a housing or handle of applicator 1306), but in some embodiments, the fiber 1304 is integrated into the applicator assembly. Since the optical fiber 1304 is non-conductive, it will not interact with the plasma beam or any high voltage components present within the applicator 1306 and is not subject to stray electrical pickup interference. In one embodiment, the optical fiber 1304 runs from the applicator 1306 to the generator unit and may be embedded in the cable that supplies power and gas flow from the generator unit to the applicator 1306.

Figure 23:
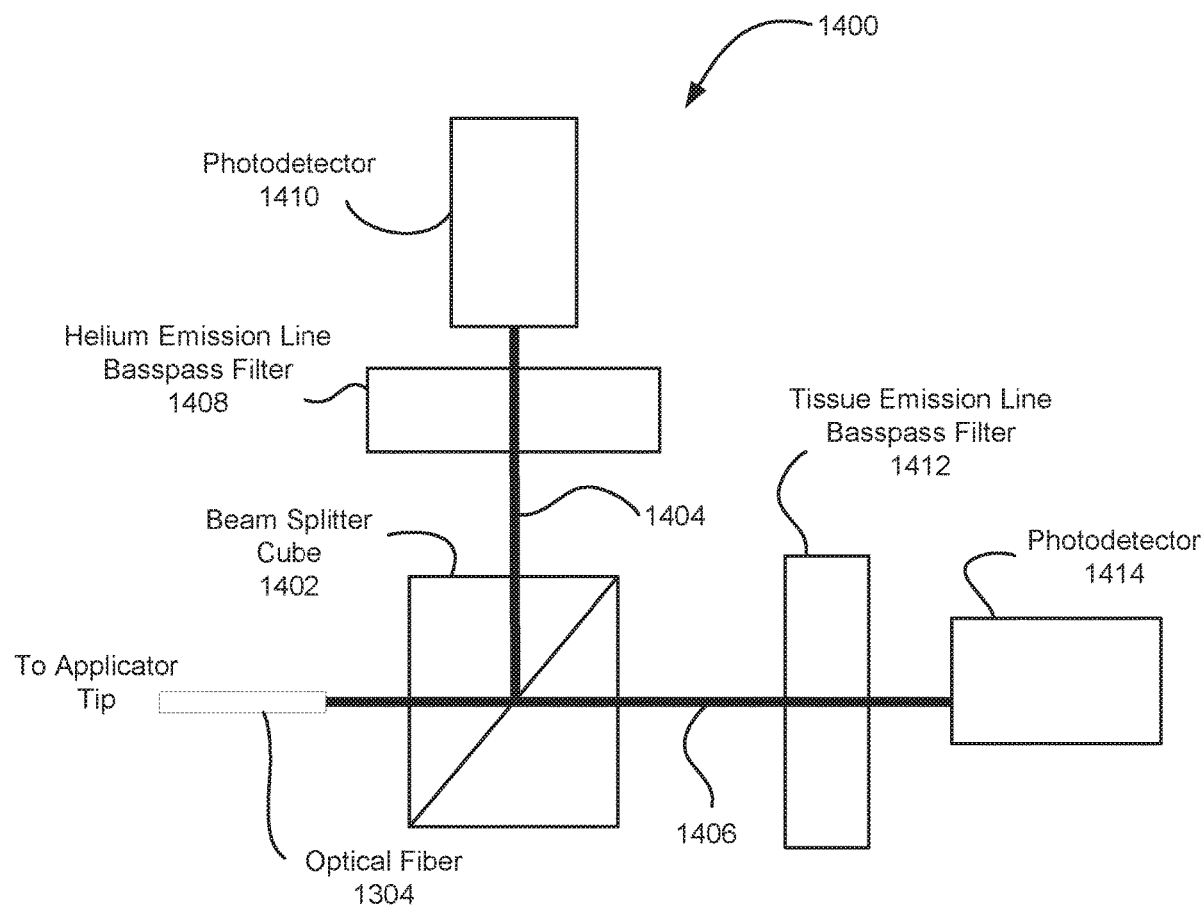
FIG. 23 illustrates an optical interface for use with the apparatus shown in FIG. 22 in accordance with an embodiment of the present disclosure.

In one embodiment, the optical fiber 1304 terminates in the generator unit with an optical interface 1400, shown in FIG. 23. In one embodiment, the optical interface 1400 takes the optical signal including the optical spectra from the fiber 1304 and passes it through a beam splitter 1402, which divides it into two paths 1404, 1406. One path 1404 is used as a reference signal. A bandpass filter 1408 filters the optical signal received from splitter 1402 and selects at least one of the emission lines or components associated with the carrier gas to be passed to photodetector 1410, with helium being used as an example in FIG. 23. Photodetector 1410 then converts this optical reference signal (including the filtered signal having the selected emission lines of the carrier gas) into an electrical reference signal. The other optical path 1406 from the beam splitter 1402 passes through a second bandpass filter 1412, selected to monitor and pass at least one of the tissue-derived emission components to photodetector 1414. Second photodetector 1414 in path 1406 converts this optical signal (including the filtered signal having the tissue-derived emission lines or components) into an electrical one. Each of the electrical signals generated by detectors 1410 are used by a controller or processor of interface 1400 (e.g., such as processor 1305) to generate the feedback signal to adjust the applied power level. In some cases, variability in the plasma beam may cause variability in the tissue-derived emission spectra and may be confused with changes in the physiological response to the plasma beam. By monitoring both the carrier gas emission intensity and the tissue-derived emission intensity simultaneously, variations in the plasma beam can be compensated for by the controller or processor (e.g., such as processor 1305) in optical interface 1400.

In the case where simply the emergence of a tissue-derived emission line is sufficient to reduce the applied power level, the beam splitter 1402, reference bandpass filter 1408 and associated photodetector 1410 may be eliminated. Only the tissue-derived emission band pass filter 1412 and its photodetector 1414 are required.

Not shown in FIG. 23 are the A/D converters to digitize the electrical output of the photodetectors, and the controller or processor which develops a feedback signal to adjust the applied power level of the generator, based on the compensated intensity of a tissue-derived optical emission. The controller or processor may be processor 1305, which may be disposed in or on applicator 1300 or in the generator.

It is to be appreciated that, although the optical interface 1400 is described as being disposed in an electrosurgical generator, in other embodiments, some or all of the components of optical interface 1400 may be disposed in applicator 1300 or a device coupled to applicator 1300.

Figure 24A:
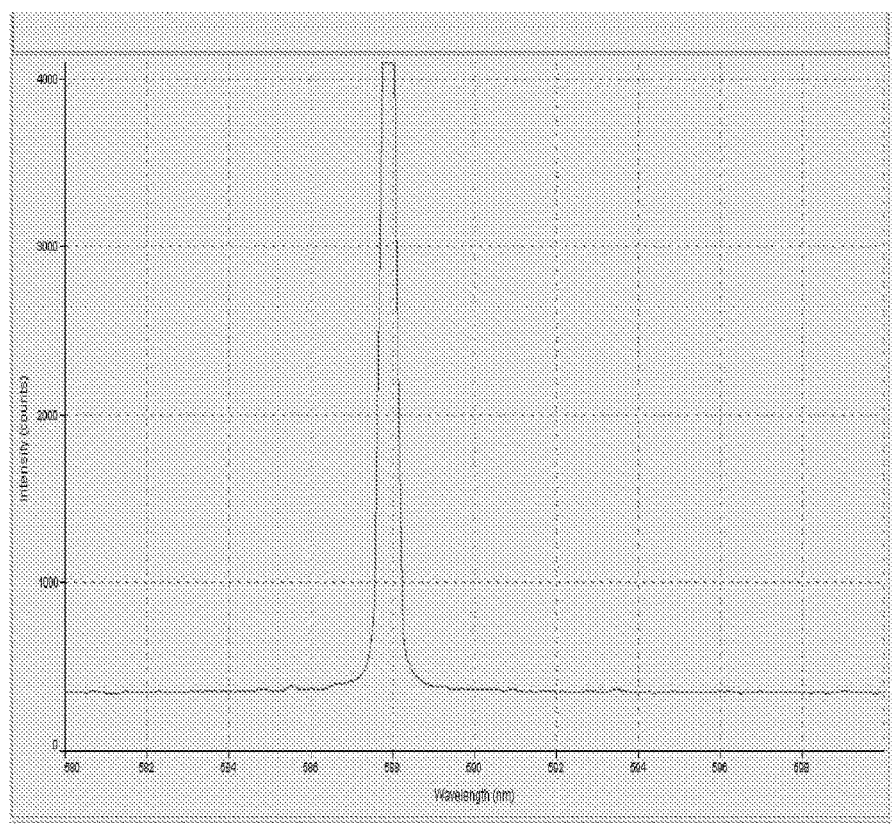
FIG. 24A and FIG. 24B illustrate exemplary tissue-derived optical emissions in accordance with an embodiment of the present disclosure.
Figure 24B:
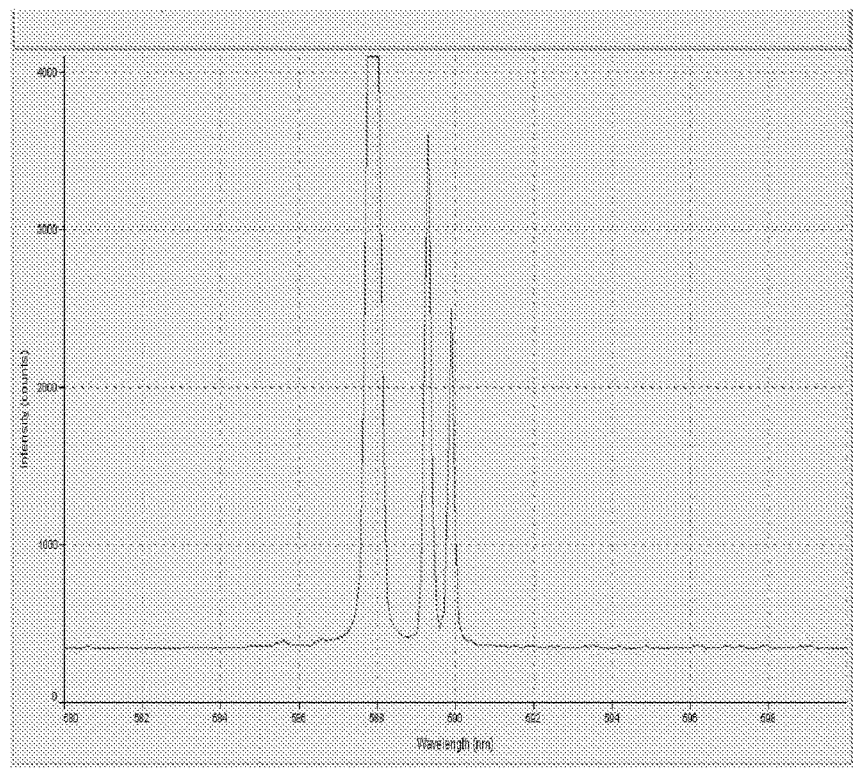

An example of the tissue-derived optical emission is shown in FIG. 24A and FIG. 24B. A plasma beam using helium flowing at 4 liters per minute, with the applicator nozzle tip placed 5 millimeters above the test tissue (chicken) and set to an applied power level of 20 Watts is scanned across the tissue surface at a constant speed of 4 millimeters per second. Part of the optical emission spectrum observed is shown in FIG. 24A, which indicates only a strong emission line of helium, centered at approximately 587.5 nanometers. When the applicator scan speed is reduced to 1 millimeter per second, increasing the applied energy density by a factor of 4, new tissue-derived emission spectral features emerge, shown in FIG. 24B. These new features are the so-called sodium "D" lines at approximately 589 and 589.6 nanometers, respectively. If the applicator scan speed is returned to the 4 millimeters per second rate, reducing the applied energy density to its earlier value, these new features disappear. The use of the sodium "D" lines as a tissue-derived optical emission spectral feature is useful since the presence of sodium chloride (salt) is ubiquitous in most tissue types.

In the embodiments described above, noise generated by the plasma discharge may be filtered out at the standoff 700, the applicator 600, or the ESU generator 12, either individually or in various combinations. In addition, the selection of measurement timing period, described below, may provide noise filtering and may be used alone or in combination with filtering at standoff 700, applicator 600, or ESU generator 12, again either individually or in various combinations.

As described above, the energy application process by applicator 600 may introduce noise into the measurements obtained by standoff device 700 and/or applicator 600 in monitoring the applied energy density during a procedure. In gathering measurements (e.g., temperature on tissue surface 506, electrical impedance of the beam 502 and target tissue, etc.) associated with the applied energy density, a controller disposed in either applicator 600, or a generator unit coupled to applicator 600, is configured to receive the obtained measurements and filter out noise within the measurements that is generated by the energy application process. For example, the controller may be configured to only use electrical impedance or acoustic measurements obtained during inter-pulse periods of beam 502 and to ignore measurements obtained outside of the inter-pulse periods. It is to be appreciated that the controller may also be configured with other filtration techniques for removing noise from the signal and such techniques are within the scope of the present disclosure.

It is to be appreciated that the various features shown and described are interchangeable, that is, a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An electrosurgical apparatus comprising:
   an applicator including a distal tip, the applicator configured for generating plasma and ejecting the generated plasma from the distal tip;
   a standoff device including an applicator receiving portion, at least one post, and a base, the at least one post coupling the applicator receiving portion to the base and the applicator receiving portion configured to receive a distal portion of the applicator such that the distal tip of the applicator is disposed through an aperture of the applicator receiving portion at a predetermined fixed distance from a tissue surface when the base contacts the tissue surface, wherein the base includes at least one sensor for monitoring at least one variable of the tissue surface, the at least one sensor configured to contact the tissue surface when the base contacts the tissue surface; and
   at least one controller configured to determine the energy density applied to the tissue surface by the plasma from the monitored at least one variable of the tissue surface by the at least one sensor and adjust an applied power level of the plasma based on the determined energy density.

2. The electrosurgical apparatus of claim 1, wherein the base is configured in a ring shape having an aperture and the distal tip is oriented such that plasma is applied through the aperture of the base to the tissue surface.

3. The electrosurgical apparatus of claim 2, wherein the base includes an outer circumference defining the aperture of the base and the at least one post is coupled to the outer circumference.

4. The electrosurgical apparatus of claim 1, wherein the at least one controller is configured to adjust the applied power level of the plasma, such that, the applied energy density to the tissue surface remains within a predetermined beneficial range that achieves a desired physiological effect.

5. The electrosurgical apparatus of claim 1, wherein the at least one controller is further configured to determine at least one of a direction or a speed of movement of the distal tip of the applicator relative to the tissue surface from the monitored at least one variable by at least two sensors.

6. The electrosurgical apparatus of claim 1, wherein the at least one sensor is an annular sensor.

7. The electrosurgical apparatus of claim 1, wherein the at least one sensor includes an array of sensors.

8. The electrosurgical apparatus of claim 7, further comprising a circuit configured to serialize measurement data received from the array of sensors and output the measurement data via a single wire to the at least one controller.

9. The electrosurgical apparatus of claim 1, wherein the at least one sensor is a temperature sensor and the at least one variable is the temperature of the tissue surface.

10. The electrosurgical apparatus of claim 1, wherein the at least one sensor includes at least first and second contact electrodes.

11. The electrosurgical apparatus of claim 10, further comprising a circuit configured to apply a probe signal to the first and second contact electrodes and measure the voltage and current of the first and second contact electrodes, the at least one controller configured to determine tissue impedance based on the voltage and current measurements of the first and second contact electrodes and the at least one variable is the determined tissue impedance.

12. The electrosurgical apparatus of claim 10, further comprising a circuit configured to apply a probe signal to the first and second contact electrodes and measure the voltage and current of the first and second contact electrodes, the at least one controller configured to determine the phase shift between the voltage and current of the first and second contact electrodes and the at least one variable is the determined phase shift.

13. The electrosurgical apparatus of claim 1, wherein the at least one sensor includes at least first and second acoustical transducers and the electrosurgical apparatus further comprises a circuit configured to apply an electrical oscillation to the first acoustical transducer, such that an acoustical emission is emitted from the first acoustical transducer into the tissue surface and received by the second acoustical transducer, the circuit further configured to determine an acoustical impedance of the tissue surface based on a distance between the first and second acoustical transducers and a time-of-flight for the acoustical emission emitted between the first and second acoustical transducers and the at least one variable is the determined acoustical impedance.

14. The electrosurgical apparatus of claim 1, wherein the at least one sensor includes at least first and second acoustical transducers and the electrosurgical apparatus further comprises a circuit configured to apply an electrical oscillation to the first acoustical transducer, such that an acoustical emission is emitted from the first acoustical transducer into the tissue surface and received by the second acoustical transducer, the circuit further configured to determine an acoustical absorption of the tissue surface based on an amplitude of the acoustical signal received by the second acoustical transducer and the at least one variable is the determined acoustical absorption.

15. The electrosurgical apparatus of claim 1, wherein the at least one sensor determines electrical impedance of the plasma and the at least one variable is the determined electrical impedance.

16. The electrosurgical apparatus of claim 1, further comprising a circuit for determining a change in phase shift between the voltage and current of the plasma and/or the tissue surface, the at least one variable is the determined change in phase shift.

17. An electrosurgical apparatus comprising:
an applicator including a distal tip, the applicator configured for generating plasma and ejecting the generated plasma from the distal tip;
a standoff device including an applicator receiving portion, at least one post, and a base, the at least one post coupling the applicator receiving portion to the base and the applicator receiving portion configured to receive a distal portion of the applicator such that the distal tip of the applicator is disposed through an aperture of the applicator receiving portion at a predetermined fixed distance from a tissue surface when the base contacts the tissue surface;
at least one two sensors disposed apart from each other on the base for monitoring at least one variable of the tissue surface, the at least two sensors configured to contact the tissue surface when the base contacts the tissue surface; and
at least one controller configured to determine the energy density applied to the tissue surface at each sensor from the monitored at least one variable of a respective sensor and to determine at least one of a direction and/or a speed of movement of the distal tip of the applicator relative to the tissue surface from the monitored at least one variable of both of the at least two sensors.

18. The electrosurgical apparatus of claim 17, wherein the at least two sensors are temperature sensors and the at least one variable is the temperature of the tissue surface.

19. The electrosurgical apparatus of claim 17, wherein the at least two sensors include at least first and second contact electrodes and the at least one variable is tissue impedance.

20. The electrosurgical apparatus of claim 19, further comprising a circuit configured to apply a probe signal to the first and second contact electrodes and measure the voltage and current of the first and second contact electrodes, the at least one controller configured to determine the tissue impedance based on the voltage and current measurements of the first and second contact electrodes.

21. The electrosurgical apparatus of claim 17, wherein the at least two sensors includes at least first and second acoustical transducers and the at least one variable is acoustical impedance.

22. The electrosurgical apparatus of claim 21, further comprising a circuit configured to apply an electrical oscillation to the first acoustical transducer, such that an acoustical emission is emitted from the first acoustical transducer into the tissue surface and received by the second acoustical transducer, the circuit further configured to determine the acoustical impedance of the tissue surface based on a distance between the first and second acoustical transducers and a time-of-flight for the acoustical emission emitted between the first and second acoustical transducers.

* * * * *